(12) United States Patent
Ryerson et al.

(10) Patent No.: US 6,346,419 B1
(45) Date of Patent: Feb. 12, 2002

(54) PHOTOLYSIS SYSTEM FOR FAST-RESPONSE $NO_2$ MEASUREMENTS AND METHOD THEREFOR

(75) Inventors: Thomas B. Ryerson, Boulder; Eric J. Williams, Lafayette, both of CO (US)

(73) Assignee: The United States of America as represented by the Department of Commerce, Washington, DC (US)

( * ) Notice: Subject to any disclaimer, the term of this patent is extended or adjusted under 35 U.S.C. 154(b) by 0 days.

(21) Appl. No.: 09/603,998

(22) Filed: Jun. 26, 2000

(51) Int. Cl.$^7$ .............................................. G01N 21/76
(52) U.S. Cl. ...................... 436/117; 436/172; 436/905; 422/52; 422/93
(58) Field of Search ............................... 436/110, 116, 436/117, 118, 172, 905; 422/52, 93, 83

(56) References Cited

U.S. PATENT DOCUMENTS

| | | | |
|---|---|---|---|
| 3,840,342 A | | 10/1974 | Neti et al. |
| 4,822,564 A | * | 4/1989 | Howard ........................ 422/52 |
| 5,571,724 A | * | 11/1996 | Johnson ........................ 436/116 |
| 5,906,946 A | * | 5/1999 | Sausa et al. ................. 436/116 |

OTHER PUBLICATIONS

Bradshaw, J. et al., Photofragmentation two–photon laser–induced fluorescence detection of NO2 and NO: comparison of measurements with model results based on airborne observations during PEM–Tropics A, Geophysical Research Letters, 26, 471–474, Feb. 15, 1999.

Butcher, S.S. et al., Effect of inlet residence time on analysis of atmospheric nitrogen oxides and ozone, Analytical Chemistry, 43:13, 1890–1892, 1971.

(List continued on next page.)

*Primary Examiner*—Jeffrey Snay
(74) *Attorney, Agent, or Firm*—Stevens, Davis, Miller & Mosher, L.L.P.

(57) ABSTRACT

An efficient, lightweight, and relatively inexpensive photolysis system based on a short-arc Hg arc lamp provides a simple and accurate method for measurement of ambient $NO_2$. High time resolution is achieved by minimizing inlet and photolysis cell residence times and matching NO and $NO_2$ sample paths, and data reduction is greatly simplified relative to conventional photolysis designs. The single-channel embodiment includes (a) a UV light source for emitting light capable of photolytically dissociating $NO_2$ in the gas sample to NO; (b) a device for positioning the light source; (c) an ellipsoidal reflector for collecting and focusing the light from the light source; (d) an enclosure for enclosing the light source and the ellipsoidal reflector; (e) an optical filter assembly for receiving, filtering, and transmitting the focused light; (f) a shutter capable of blocking the transmission of the filtered light which is transmitted through the optical filter assembly; (g) a sample photolysis cell for containing a volume of the gas sample; (h) a device for controllably introducing the gas sample to the sample photolysis cell, and a device for controllably delivering the gas sample from the sample photolysis cell; (i) a detector capable of detecting an amount of the NO present in the gas sample delivered from the sample photolysis cell, and capable of emitting a signal representative of the amount of NO; and (j) a device for measuring the signal so as to quantify the amount of NO. The system is characterized by i) higher conversion efficiency at faster time response; ii) lower power consumption; iii) less heat output with consequently less sample heating; iv) optically filtered light output for $NO_2$-specific conversion, and v) simplified data reduction. The system can be used for measurement of gas-phase $NO_2$ at concentrations ranging from parts per trillion to parts per million or higher. Present applications of the system include ambient atmospheric air measurements, while future medical applications might include the non-invasive monitoring of human breath for $NO_2$.

27 Claims, 4 Drawing Sheets

OTHER PUBLICATIONS

Del Negro, L.A. et al., Comparison of modeled and observed values of NO2 and JNO2 during the Photochemistry of Ozone Loss in the Arctic Region in Summer (POLARIS) mission, Journal of Geophysical Research, vol. 104, No. D21, pp. 26,687–26,703, Nov. 20, 1999.

DeMore, W.B. et al., Chemical Kinetics and Photochemical Data for Use in Stratospheric Modeling, Evaluation No. 12, NASA Jet Propulsion Laboratory, California Institute of Technology, Pasadena, California, 1997, pp. i–ix, 1, 18–20, 51–53.

Fehsenfeld, F.C. et al., Intercomparison of NO2 measurement techniques, Journal of Geophysical Research, vol. 95, No. D4, pp. 3579–3597, Mar. 20, 1990.

Fehsenfeld, F.C. et al., Ground–based intercomparison of nitric acid measurement techniques, Journal of Geophysical Research, vol. 103, No. D3, pp. 3343–3353, Feb. 20, 1998.

Gao, R.S. et al., Partitioning of the reactive nitrogen reservoir in the lower stratosphere of the southern hemisphere: Observations and modeling, Journal of Geophysical Research, vol. 102, No. D3, pp. 3935–3949, Feb. 20, 1997.

Gao, R.S. et al., New photolysis system for NO2 measurements in the lower stratosphere, Journal of Geophysical Research, vol. 99, No. D10, pp. 20,673–20,681, Oct. 20, 1994.

Gillani, N.V. et al., Relative production of ozone and nitrates in urban and rural power plant plumes 1. Composite results based on data from 10 field measurement days, Journal of Geophysical Research, vol. 103, No. D17, pp. 22,593–22, 615, Sep. 20, 1998.

Huey, L.G. et al., Fast time response measurements of HNO3 in air with a chemical ionization mass spectrometer, Journal of Geophysical Research, vol. 103, No. D3, pp. 3355–3360, Feb. 20, 1998.

Kley, D. et al., Chemiluminescence detector for NO and NO2, Atmospheric Technology, 12, 63–69, 1980.

Luria, M. et al., The evolution of photochemical smog in a power plant plume, Atmospheric Environment, 33, 3023–3036, 1999.

Mihelcic, D. et al., An improved method of measuring tropospheric NO2 and RO2 by matrix isolation and electron spin resonance, Journal of Atmospheric Chemistry, 3, 341–361, 1985.

Pätz, H.–W. et al., Measurements of trace gases and photolysis frequencies during SLOPE96 and a coarse estimate of the local OH concentration from HNO3 formation, Journal of Geophysical Research, vol. 105, No. D1, pp. 1563–1583, Jan. 20, 2000.

Ridley, B.A. et al., NO and NO2 in the troposphere: technique and measurements in regions of a folded tropopause, Journal of Geophysical Research, vol. 93, No. D12, pp. 15,813–15,830, Dec. 20, 1988.

Ridley, B. et al., Is the Arctic surface layer a source and sink of NOx in Winter/Spring?, Journal of Atmospheric Chemistry, 36, 1–22, 2000.

Roberts, J.M. et al., Measurements of PAN, PPN, and MPAN made during the 1994 and 1995 Nashville Intensives of the Southern Oxidant Study: Implications for regional ozone production from biogenic hydrocarbons, Journal of Geophysical Research, vol. 103, No. D17, pp. 22,473–22, 490, Sep. 20, 1998.

Ryerson, T.B. et al., Emissions lifetimes and ozone formation in power plant plumes, Journal of Geophysical Research, vol. 103, No. D17, pp. 22,569–22,583, Sep. 20, 1998.

Sandholm, S.T. et al., An airborne compatible photofragmentation two–photon laser–induced fluorescence instrument for measuring background tropospheric levels of NO, NOx, and NO2, Journal of Geophysical Research, vol. 95, No. D7, pp. 10,155–10,161, Jun. 30, 1990.

Shetter, R.E. et al., Photolysis frequency measurements using actinic flux spectroradiometry during the PEM–Tropics mission: Instrumentation description and some results, Journal of Geophysical Research, vol. 104, No. D5, pp. 5647–5661, Mar. 20, 1999.

Tanner, R.L. et al., Measuring inorganic nitrate species with short time resolution from an aircraft platfrom by dual–channel ozone chemiluminescence, Journal of Geophysical Research, vol. 103, No. D17, pp. 22,387–22,395, Sep. 20, 1998.

Wang, T. et al., Ground–based measurements of NOx and total reactive oxidized nitrogen (NOy) at Sable Island, Nova Scotia, during the NARE 1993 summer intensive, Journal of Geophysical Research, vol. 101, No. D22, pp. 28,991–29, 004, Dec. 20, 1996.

Wayne, R.P. et al., The nitrate radical: physics, chemistry, and the atmosphere, Atmospheric Environment, vol. 25A No. 1, pp. 1, v, 2, 36–50, 191–203, 1991.

P.A. Leighton, Photochemistry of Air Pollution, Academic Press, 1961.

M. J. Bollinger, Chemiluminescent measurement of the oxides of nitrogen, etc., Doctoral thesis, University of Colorado, 1982, cover page, pp. 26–30, 41–50.

* cited by examiner

PHOTOLYSIS SYSTEM FOR FAST-RESPONSE NO₂ MEASUREMENTS AND METHOD THEREFOR

The invention described herein may be manufactured, used, and licensed by the U.S. Government for governmental purposes without the payment of any royalties thereon.

BACKGROUND OF THE INVENTION

1. Field of the Invention

This invention relates generally to a system and a method for measuring a quantity of $NO_2$ in a gas sample. The invention relates more specifically to a system and a method which employ ultraviolet light to effect the photolytic dissociation of $NO_2$ to NO.

2. Description of Related Art

Improved understanding of human-induced and natural atmospheric chemistry requires a sensitive and specific measurement of $NO_2$, a molecule which is a key species in atmospheric ozone formation and loss processes. An ideal measurement of $NO_2$ would be inexpensive and simple to operate, while providing quality data at high time resolution.

Most conventional commercially available instruments used for measuring $NO_2$ in the atmosphere employ hot metal catalysts for $NO_2$ conversion. These conventional devices, however, are not specific for $NO_2$.

For example, one commercially available converter design is based on the reduction of $NO_2$ to NO on a heated substrate (i.e., thermal decomposition), typically molybdenum oxide or, less of ten, ferrous sulfate. These surface-based converters are not specific for $NO_2$, as they also efficiently reduce other atmospheric nitrogen-containing compounds to a detectable form. (Fehsenfeld, F. C., et al., Intercomparison of $NO_2$ measurement techniques, Journal of Geophysical Research, 95, 3579–3597, 1990; Fehsenfeld, F. C., et al., Ground-based intercomparison of nitric acid measurement techniques, Journal of Geophysical Research, 103, 3343–3353, 1998.) Use of these converters can result in a gross overestimate of ambient $NO_2$.

Another technique, the photolytic dissociation of $NO_2$ with UV light, followed by chemiluminescence detection of the product NO, has been employed for ambient measurements of $NO_2$ for over two decades. (Kley, D., et al., Chemiluminescence detector for NO and $NO_2$, Atmospheric Technology, 12, 63–69, 1980.) This broadband photolysis technique has provided field measurement data used to evaluate and improve the current understanding of tropospheric and stratospheric ozone chemistry, radiative transfer, and sources and fate of reactive nitrogen compounds. The photolysis-chemiluminescence (P-CL) technique has been compared to other $NO_2$ measurement techniques on the ground (Mihelcic, D., et al., An improved method of measuring tropospheric $NO_2$ and $RO_2$ by matrix isolation and electron spin resonance, Journal of Atmospheric Chemistry, 3, 341–361, 1985.; Fehsenfeld et al., 1990) and aboard aircraft (Del Negro, L. A., et al., Comparison of modeled and observed values of $NO_2$ and $J_{NO2}$ during the Photochemistry of Ozone Loss in the Arctic Region in Summer (POLARIS) mission, Journal of Geophysical Research, 104, 26, 687–26, 703, 1999), and been shown to provide useful data over a wide range of concentrations, ambient environments, and integration times.

$NO_2$ is photodissociated at ultraviolet (UV) wavelengths below about 420 nm in a first-order process, $$NO_2 + h\nu \rightarrow NO + O \qquad (1)$$

with the rate constant for photolysis given by j (units of $s^{-1}$), which is the wavelength-integrated product of the photon flux (photons $cm^{-2}s^{-1}$), the weakly temperature-dependent $NO_2$ absorption cross-section ($cm^2$ $molecule^{-1}$), and the quantum yield for photodissociation (molecules $photon^{-1}$) (DeMore, W. B., et al., Chemical Kinetics and Photochemical Data for use in Stratospheric Modeling, NASA Jet Propulsion Laboratory, Pasadena, Calif., 1997). In air, the O atom formed in (1) reacts rapidly with molecular oxygen to form $O_3$:

$$O + O_2 \rightarrow O_3 \qquad (2)$$

which can then react with NO to re-form $NO_2$:

$$NO + O_3 \rightarrow NO_2 + O_2 \qquad (3)$$

with the second-order rate constant for (3) given by k ($cm^3$ $molecule^{-1}s^{-1}$). During the daytime in the atmosphere, a photostationary state (characterized by zero net concentration change occurring over time) is established via these coupled reactions (Leighton, P. A., Photochemistry of Air Pollution, Academic Press, New York, 1961). Under daytime conditions, a new photostationary state will be established within 1–2 minutes of a perturbation to j or to the concentrations of the chemical species listed above.

Significant changes to concentrations of these coupled species can therefore occur during measurement, a result of perturbing the j value when ambient air is sampled into an instrument (Butcher, S. S., et al., Effect of inlet residence time on analysis of atmospheric nitrogen oxides and ozone, Analytical Chemistry, 43, 1890–1892, 1971; Bollinger, M. J., Chemiluminescent measurements of the oxides of nitrogen in the clean troposphere and atmospheric chemistry implications, Doctoral thesis, University of Colorado, Boulder, Boulder, 1982; Ridley, B. A., et al., NO and $NO_2$ in the troposphere: technique and measurements in regions of a folded tropopause, Journal of Geophysical Research, 93, 15, 813–15, 830, 1988; Parrish, D. D., et al., Systematic variations in the concentration of NOx (NO plus $NO_2$) at Niwot Ridge, Colorado, Journal of Geophysical Research, 95, 1817–1836, 1990). This occurs despite the minimal surface loss on most materials exhibited by these species. If total instrument sample residence times, from inlet tip to detector, are greater than a second or so, non-negligible bias in the derived concentrations of NO, $NO_2$, and $O_3$ can result from reactions (1) through (3) occurring during sampling.

The presence of other ambient oxidants (e.g., $HO_2$ or $RO_2$ species), or the occurrence of surface-induced oxidation of NO (Ridley et al., 1988), act to increase this bias. Data reduction procedures have been developed to account for reactions (1) through (3) during sampling and are relevant to all NO, $NO_2$, and $O_3$ measurements except open-path designs [Kley et al., 1980; Bollinger, 1982; Ridley et al., 1988; Parrish et al., 1990). These procedures were developed assuming pseudo-first-order conditions, i.e., that ozone is in large excess relative to NO and $NO_2$, and that peroxy radical concentrations are negligibly small. These assumptions do not necessarily apply in many urban areas and in power plant plumes, as indicated in the $NO_2$ Data Reduction section, below.

Reaction (1) is exploited in the P-CL measurement to photodissociate $NO_2$ to NO, and the resulting product NO is measured as an increase in chemiluminescence signal above that from ambient NO (Kley et al., 1980). Ambient $NO_2$ concentrations are derived from the difference between two signals, both of which can be large and vary quite rapidly under changing atmospheric conditions. Efficient conversion of $NO_2$ to NO serves to maximize that difference and improve instrumental sensitivity for $NO_2$.

In sampled ambient air, the effective conversion fraction (CF) of $NO_2$ is given by (Bollinger, 1982), $$CF=[j\tau/(j\tau+k[Ox]\tau)]*[1-exp(-j\tau-k[Ox]\tau)] \quad (4)$$

where j is the wavelength-integrated product of the $NO_2$ absorption cross-section, the light source flux, and the quantum yield for photodissociation; $\tau$ is the sample residence time in the photolysis cell (Kley et al., 1980). The light source flux, and thus j, is determined by the choice of lamp, reflector and filter optics, and cell geometry. Here k[Ox] denotes the rate coefficient and concentration of any oxidant that reacts with NO to produce $NO_2$ in the cell.

Examination of (4) shows that increasing j without increasing r is the most effective way of maximizing instrumental sensitivity to $NO_2$. This is illustrated graphically in FIG. 3, which shows CF calculated from (4) at 298 K as a function of cell residence time and ambient ozone concentration for j values ranging over a factor of nine. Higher j values confer the additional benefit of decreasing CF dependence on variations in ambient oxidant levels (FIG. 3). Further, the magnitude of the correction for changes in NO, $NO_2$, and $O_3$ concentrations during sampling is reduced at higher j values (e.g., Ridley et al., 1988).

Equally important is that (4) holds during sample transit in inlet tubing, where j~0 (Butcher et al., 1971). Correctly accounting for loss of NO and $O_3$ and the formation of $NO_2$ during the entire sampling process, including transit through inlet lines, is critical for accurate retrieval of ambient NO, $NO_2$, and $O_3$ mixing ratios from measured data. Neglect of reaction (3) in data analysis results in a systematic error in the determination of $NO_2$; this error is dependent on ambient oxidant levels and ranges from 10 to 20% at sample residence times of 3 seconds or more. The sampling issues mentioned above can be significantly minimized by decreasing instrumental sample residence times (Ridley et al., 1988). Thus, increasing j and minimizing $\tau$ in the inlet and photolysis cell dramatically improves instrument accuracy and simplicity of data reduction in P-CL instruments.

Additional benefits of short sample residence times come in the form of increased instrumental time resolution and potentially enhanced specificity for $NO_2$. Time resolution in well-designed P-CL systems is limited by longitudinal diffusion and mixing in the photolysis cell. Undesired sample mixing during longer cell residence times acts as a low-pass filter on high-frequency variations in ambient $NO_2$, so that peak amplitudes are attenuated and information is lost (Ridley et al., 1994). Short instrumental sample residence times tend to minimize unwanted conversion of other nitrogen-containing species to detectable forms (e.g., Gao, R. S., et al., New photolysis system for $NO_2$ measurements in the lower stratosphere, Journal of Geophysical Research, 99, 20, 673–20, 681, 1994). Operational photolysis systems represent compromises between conversion efficiency, time resolution, and specificity for $NO_2$.

Both broadband and monochromatic light sources have been used to effect photolysis of $NO_2$. For example, in a broadband technique, U.S. Pat. No. 3,840,342 describes a method of converting $NO_2$ to NO which includes maintaining the $NO_2$ at a temperature from about 40° C. to about 130° C. while exposing the $NO_2$ to ultraviolet radiation.

The spectrally narrow output of XeF (353 nm) or Nd:YAG (355 nm) lasers have been used in an aircraft $NO_2$ instrument (Sandholm, S. T., et al., An airborne compatible photofragmentation two-photon laser-induced fluorescence instrument for measuring background tropospheric levels of NO, $NO_x$, and $NO_2$, *Journal of Geophysical Research*, 95, 10155–10161, 1990; Bradshaw, J., et al., Photofragmentation two-photon laser-induced fluorescence detection of $NO_2$ and NO: comparison of measurements with model results based on airborne observations during PEM-Tropics A, *Geophysical Research Letters*, 26, 471–474, 1999). While offering potentially large increases in specificity and sensitivity, laser photolysis systems are not yet widely utilized due in part to their relative complexity, size, weight, and cost.

At present, standard photolytic designs typically utilize the UV output of a collimated 300W or 500W direct-current (DC) short-arc Xe lamp to effect conversion (Kley et al., 1980; Ridley et al., 1988). Lamp ignition is accomplished by a very high (25 kV) voltage pulse, although the operating voltage is much lower (12–15 v DC). The short-arc Xe discharge approximates a point source, and emitted light is easily collimated by a rear parabolic reflector integral to the lamp body. Optimized systems using these lamps have reported a photodissociation rate constant (j value) of ~0.37 $s^{-1}$, providing a calculated CF=0.31 in a cell residence time of 1 s (Kley et al., 1980). Longer cell residence times are typically chosen, affording increased $NO_2$ sensitivity at the expense of instrument time response; at $\tau$=4 to 5 s, these systems exhibit a CF~0.50 (Parrish et al., 1990; Ridley et al., 1994). Useful power output between 320 and 420 nm is about 3 W, or 1% of the total power dissipated by the lamp (Gao et al., 1994).

These lamps emit strongly in the infrared (IR) region, and dielectric mirrors are always used to prevent IR wavelengths from entering the cell. In many designs the photolysis cell is cooled below ambient temperatures to further reduce interferences from thermal decomposition of other nitrogen-containing species during sampling. Published reports of measured conversion fractions for $NO_2$ range from 0.25 to 0.6 in cell residence times of 2 to 5 s, corresponding to an effective j value approaching 0.2 $s^{-1}$. Complete P-CL instruments utilizing 500W or 1000W Xe lamps are marketed commercially (Eco-Physics, Ann Arbor, Mich.).

More recently, a P-CL system based on a 400W DC long-arc metal-halide lamp has been used to provide $NO_2$ measurements (Gao et al., 1994; Gao, R. S., et al., Partitioning of the reactive nitrogen reservoir in the lower stratosphere of the southern hemisphere: Observations and modeling, *Journal of Geophysical Research*, 102, 3935–3949, 1997; Del Negro et al., 1999). Several improvements over the Xe lamp systems were demonstrated. Lamp ignition voltage is much lower, between 1 and 2 kV, and the operating voltage is roughly 120 v AC. Nearly 65W, or 16% of total power dissipated is emitted at useful (320 to 400 nm) wavelengths. Optical filters in the beam path are used to minimize undesirable thermolytic and photolytic conversion of other atmospheric species to detectable forms; the optical filters also attenuate roughly 40% of usable light. With filters in place, conversion fractions of 0.56 in cell residence times of 1.1 s were achieved. This system is characterized by an effective j value of 0.75 $s^{-1}$, which is a significant improvement over a Xe system of equivalent wattage (Del Negro et al., 1999).

The metal-halide lamp source is diffuse, approximating a line source, and requires an external dielectric mirror to reflect emitted UV light into the cell. The physically large photolysis cell (i.e., 5 cm i.d.×25 cm long) is well-matched to the lamp-reflector combination, and a 1.1 s sample residence time is obtained by reducing the cell pressure to ~30 Torr. The lamp electrodes, optical filters, and cell are cooled by forced ambient stratospheric air initially at −50°

C. Without active cooling, the filter set would be destroyed by thermal stresses induced by the intense IR emissions from the lamp (Gao et al., 1994).

There are, therefore, size, cost, and thermal management issues attendant to conventional higher-wattage Xe or metal-halide arc lamp systems.

Therefore, a general need exists to provide a system and a method which employ ultraviolet light to effect the photolytic dissociation of $NO_2$ to NO in a simple and efficient manner. A more specific need exists for a system and a method which overcome the aforementioned size, cost, thermal management, and data retrieval at high time resolution issues associated with conventional technologies.

SUMMARY OF THE INVENTION

It is an object of the present invention to provide a system and a method which employ ultraviolet light to effect the photolytic dissociation of $NO_2$ to NO in a simple and efficient manner. It is a further object of the present invention to provide a system and a method characterized by i) higher conversion efficiency at faster time response; ii) lower power consumption; iii) less heat output with consequently less sample heating; iv) optically filtered light output for $NO_2$-specific conversion, and v) simplified data reduction.

The present invention provides an efficient, lightweight, low-power $NO_2$ photolytic converter suitable for laboratory, ground-, and aircraft-based field measurements. Conversion of $NO_2$ to NO is accomplished by focusing the output from a Hg arc lamp into a photolysis cell maintained at subambient pressure. Recovery of ambient data is facilitated by minimizing and matching NO and $NO_2$ instrument sample residence times in this multi-channel instrument, so that ambient $NO_2$ may be easily retrieved at high time resolution. Specificity is enhanced by optically filtering the lamp output to minimize unwanted conversion of other ambient species characterized by photolysis cross-sections significantly different from $NO_2$. Optical filtering also greatly reduces the spurious (or artifact) signal when sampling $NO_2$-free air.

Accordingly, in a first preferred embodiment the present invention advantageously relates to a single-channel photolysis system for measuring a quantity of $NO_2$ in a gas sample. The single-channel photolysis system comprises (a) a UV light source for emitting light capable of photolytically dissociating $NO_2$ in the gas sample to NO; (b) a means for positioning the light source; (c) an ellipsoidal reflector for collecting and focusing the light from the light source; (d) an enclosure for enclosing the light source and the ellipsoidal reflector; (e) an optical filter assembly for receiving, filtering, and transmitting the focused light from the ellipsoidal reflector; (f) a shutter capable of blocking the transmission of the filtered light which is transmitted through the optical filter assembly; (g) a sample photolysis cell for containing a volume of the gas sample; (h) a means for controllably introducing the gas sample to the sample photolysis cell, and a means for controllably delivering the gas sample from the sample photolysis cell; (i) a detector capable of detecting an amount of the NO present in the gas sample delivered from the sample photolysis cell, and capable of emitting a signal representative of the amount of NO; and (j) a means for measuring the signal so as to quantify the amount of NO.

The invention further relates to a method of measuring a quantity of $NO_2$ in a gas sample with the aforementioned single-channel photolysis system. In a typical embodiment, the method comprises the steps of (a) introducing a first portion of the gas sample to the sample photolysis cell; (b) irradiating the first portion of the gas sample with the light capable of photolytically dissociating $NO_2$; (c) delivering the first portion of the gas sample from the sample photolysis cell to the detector so as to detect the amount of NO (comprising ambient NO and that NO formed by photolysis of ambient $NO_2$) present in the first portion of the gas sample, and so as to emit the signal representative of the first portion amount of NO; (d) measuring the signal so as to quantify the first portion amount of NO; (e) positioning the shutter so as to block the transmission of the filtered light to the sample photolysis cell; (f) introducing a second portion of the gas sample to the sample photolysis cell; (g) delivering the second portion of the gas sample from the sample photolysis cell to the detector so as to detect the amount of NO present in the second portion of the gas sample, and so as to emit the signal representative of the second portion amount of NO; (h) measuring the signal so as to quantify the second portion amount of NO; and (i) positioning the shutter so as to allow the transmission of the filtered light to the sample photolysis cell.

In a second preferred embodiment the present invention advantageously relates to a dual-channel system for measuring a quantity of $NO_2$. The dual-channel photolysis system comprises a gas inlet line for receiving a total gas sample; a flow divider for dividing the total gas sample into a first gas sample having a first gas sample volume, and a second gas sample having a second gas sample volume, the first gas sample volume and the second gas sample volume being equal; a first channel for detecting ambient NO in the first gas sample; and a second channel for detecting both ambient NO, and NO resulting from the photolytic dissociation of $NO_2$ to NO, in the second gas sample.

In the dual-channel system, the first channel comprises (a) an opaque sample cell; (b) a first channel means for controllably introducing the first gas sample to the opaque sample cell, and a first channel means for controllably delivering the first gas sample from the opaque sample cell; (c) a first channel detector capable of detecting an amount of NO present in the first gas sample delivered from the opaque sample cell, and capable of emitting a signal representative of the amount of NO in the first gas sample; and (d) a first channel means for measuring the signal so as to quantify the amount of NO in the first gas sample.

In the dual-channel system, the second channel comprises (e) a UV light source for emitting light capable of photolytically dissociating $NO_2$ in the second gas sample to NO; (f) a means for positioning the light source; (g) an ellipsoidal reflector for collecting and focusing the light from the light source; (h) an enclosure for enclosing the light source and the ellipsoidal reflector; (i) an optical filter assembly for receiving, filtering, and transmitting the focused light from the ellipsoidal reflector; (j) a shutter capable of blocking the transmission of the filtered light which is transmitted through the optical filter assembly; (k) a sample photolysis cell for containing a volume of the second gas sample; (l) a second channel means for controllably introducing the second gas sample to the sample photolysis cell, and a second channel means for controllably delivering the second gas sample from the sample photolysis cell; (m) a second channel detector capable of detecting an amount of NO present in the second gas sample delivered from the sample photolysis cell, and capable of emitting a signal representative of the amount of NO in the second gas sample; and (n) a second channel means for measuring the signal so as to quantify the amount of NO in the second gas sample.

In the dual-channel system, the first channel means for controllably introducing the gas sample, the opaque sample cell, the first channel means for controllably delivering the gas sample, and the first channel detector capable of detecting an amount of NO define a first channel gas flow volume. The second channel means for controllably introducing the gas sample, the sample photolysis cell, the second channel means for controllably delivering the gas sample, and the second channel detector capable of detecting an amount of NO define a second channel gas flow volume. The first channel gas flow volume, and the second channel gas flow volume, are minimal and equal.

The invention further relates to a method of measuring a quantity of $NO_2$ in a gas sample with the aforementioned dual-channel photolysis system. In atypical embodiment, the method comprises the steps of, in the first channel, (a) introducing the first gas sample to the opaque sample cell; (b) delivering the first gas sample from the opaque sample cell to the first channel detector so as to detect the amount of NO present in the first gas sample, and so as to emit the signal representative of the amount of NO in the first gas sample; and (c) measuring the signal so as to quantify the amount of NO in the first gas sample.

In the second channel, the method comprises the steps of (d) introducing a first portion of the second gas sample to the sample photolysis cell; (e) irradiating the first portion of the second gas sample with the light capable of photolytically dissociating $NO_2$; (f) delivering the first portion of the second gas sample from the sample photolysis cell to the second channel detector so as to detect the amount of NO (comprising ambient NO and that NO formed by photolysis of ambient $NO_2$) present in the first portion of the second gas sample, and so as to emit the signal representative of the first portion amount of NO; (g) measuring the signal so as to quantify the first portion amount of NO; (h) positioning the shutter so as to block the transmission of the filtered light to the sample photolysis cell; (i) introducing a second portion of the second gas sample to the sample photolysis cell; (j) delivering the second portion of the second gas sample from the sample photolysis cell to the second channel detector so as to detect the amount of NO present in the second portion of the second gas sample, and so as to emit the signal representative of the second portion amount of NO; (k) measuring the signal so as to quantify the second portion amount of NO; and (l) positioning the shutter so as to allow the transmission of the filtered light to the sample photolysis cell.

In the method of measuring with the dual-channel system, steps (a) through (c) are performed simultaneous with said steps (d) through (l).

Use of a 200W Hg lamp in the system provides conversion fractions of $NO_2$ to NO greater than 0.70 in cell residence times of less than a second. Limiting lamp output to wavelengths greater than 350 nm by means of optical filters increases specificity for $NO_2$, affording a peroxyacetyl nitrate (PAN) conversion fraction of less than 0.006 and negligible conversion of nitric acid ($HNO_3$). Unwanted (i.e., artifact) signal in clean synthetic air is also greatly minimized through the use of optical filters.

Fast instrument response is attained by minimizing $NO_2$ inlet line and photolysis cell residence times. NO and $NO_2$ sample residence times are matched in the dual-channel instrument, so that signal from ambient NO may be easily subtracted from the total signal and ambient $NO_2$ calculated by difference at high time resolution. Induced change in the ambient ratio of NO to $NO_2$, due to reaction of ozone and other oxidants with NO during sampling, is minimized in the system. This configuration permits simple and accurate retrieval of $NO_2$ concentrations in conditions marked by extreme atmospheric variability, where ambient NO concentrations can change over several orders of magnitude in seconds. The system has been demonstrated to be more efficient, more sensitive, less subject to interferences, and simpler than previous photolytic designs. In addition, the system is much less expensive to purchase and operate than conventional designs.

In summary, the advantages associated with the embodiments of the present system and method are numerous. Generally, the invention facilitates more efficient, more specific, and simpler $NO_2$ detection, with significantly improved time response, as compared to previous P-CL designs.

First, the system enables the use of a short-arc high-pressure Hg lamp. This provides approximately a factor of 5 increase in UV output, and a factor of 4 decrease in undesired IR output, per watt of power dissipated relative to a standard Xe lamp. Increased efficiency permits significantly enhanced sensitivity, increased time resolution, and minimizes sample heating. As most of the useful power from the Hg lamp comes in a relatively narrow band of wavelengths centered around 365 nm, optical filtering provides increased specificity for $NO_2$ without undue reduction of conversion efficiency. In addition, the point-source character of the Hg lamps permits efficient collection of the emitted light.

Secondly, the system provides for focusing the lamp output. Enhanced efficiency is attained by focusing lamp output into the sample photolysis cell, thereby significantly increasing the photon flux (j value in Equation 4). This improves upon previous photolytic converter systems in which lamp output is collimated.

Thirdly, the system uses an ellipsoidal mirror external to the lamp. Locating the Hg lamp arc at one focus of a fast (i.e., f/2 or better) external ellipsoidal mirror collects nearly 80% of total emitted light. For comparison, a laboratory mirror and lens system using the same lamp collects only about 10–20% of the lamp output. The external ellipsoidal mirror is not subject to optical surface degradation from sputtered electrode material during lamp ignition and operation, is much less subject to distortion at typical operating temperatures, and permits easy realignment of the arc at the mirror focus. None of these advantages is afforded by the Xe lamps used in the conventional $NO_2$ photolysis converters, which are characterized by internal parabolic reflectors integrated with the discharge electrodes.

Fourthly, the system changes the aspect ratio of the sample cell so as to increase time response. Use of a relatively small-diameter and long sample cell minimizes longitudinal diffusion during sample transit, preserving high-frequency variations in ambient $NO_2$. Previous sample cell designs are matched to physically larger lamps and spot sizes, are characterized by larger diameter-to-length ratios, and result in more complete attenuation of high-frequency data.

Finally, the dual-channel embodiment of the system matches NO and $NO_2$ sample flow paths in a two-channel instrument. Matching sample paths permits greatly simplified data reduction procedures, and significantly enhances the time resolution attained by the $NO_2$ measurement. For the first time, $NO_2$ measurements by P-CL can be obtained on timescales equal to or faster than the sample cell residence time. Improved time resolution, at 1 second or better, in the present system extends the measurement of $NO_2$ to new areas, such as studying turbulent fluxes of $NO_2$ and quantifying ambient concentrations in power plant emission plumes. Previous measurements made with conventional devices could only retrieve data on timescales longer than the sample cell residence time, and were subject to large uncertainties under conditions of high atmospheric variability.

The applications of the photolytic system are varied and numerous. The system can be used, in conjunction with an NO detector, as a specific measurement of gas-phase $NO_2$ at concentrations ranging from parts per trillion to parts per million or higher. Current uses involve ambient atmospheric air measurements for research or regulatory purposes, the study of gas-phase reaction kinetics in a laboratory setting, and a wide variety of industrial process monitoring applications. A variety of potential future medical applications might involve the non-invasive monitoring of human breath for $NO_2$.

Thus, the present invention provides a system and a method which are superior to the aforementioned conventional devices, because it is characterized by i) higher conversion efficiency at faster time response; ii) lower power consumption; iii) less heat output with consequently less sample heating; and iv) optically filtered light output for $NO_2$-specific conversion.

The present invention has a much more efficient light source in the wavelength region of interest, and a much more efficient external reflective focusing system than any conventional system. This combination provides the key feature of high $NO_2$ conversion efficiency at high time resolution.

BRIEF DESCRIPTION OF THE DRAWINGS

Other objects, features, and advantages of the present invention will become more fully apparent from the following detailed description of the preferred embodiments and the accompanying drawings. As depicted in the attached drawings:

FIG. 6b is a depiction of retrieved mixing ratio data, averaged to 1-s intervals, for the plume transect depicted in FIG. 6a.

DESCRIPTION OF THE PREFERRED EMBODIMENTS

The present invention will be disclosed in terms of the currently perceived preferred embodiments thereof.

The various embodiments of the present invention provide a system and a method for measuring a quantity of $NO_2$ in a gas sample.

Accordingly, in a first preferred embodiment the present invention advantageously relates to a single-channel photolysis system for measuring a quantity of $NO_2$ in a gas sample.

Figure 1:
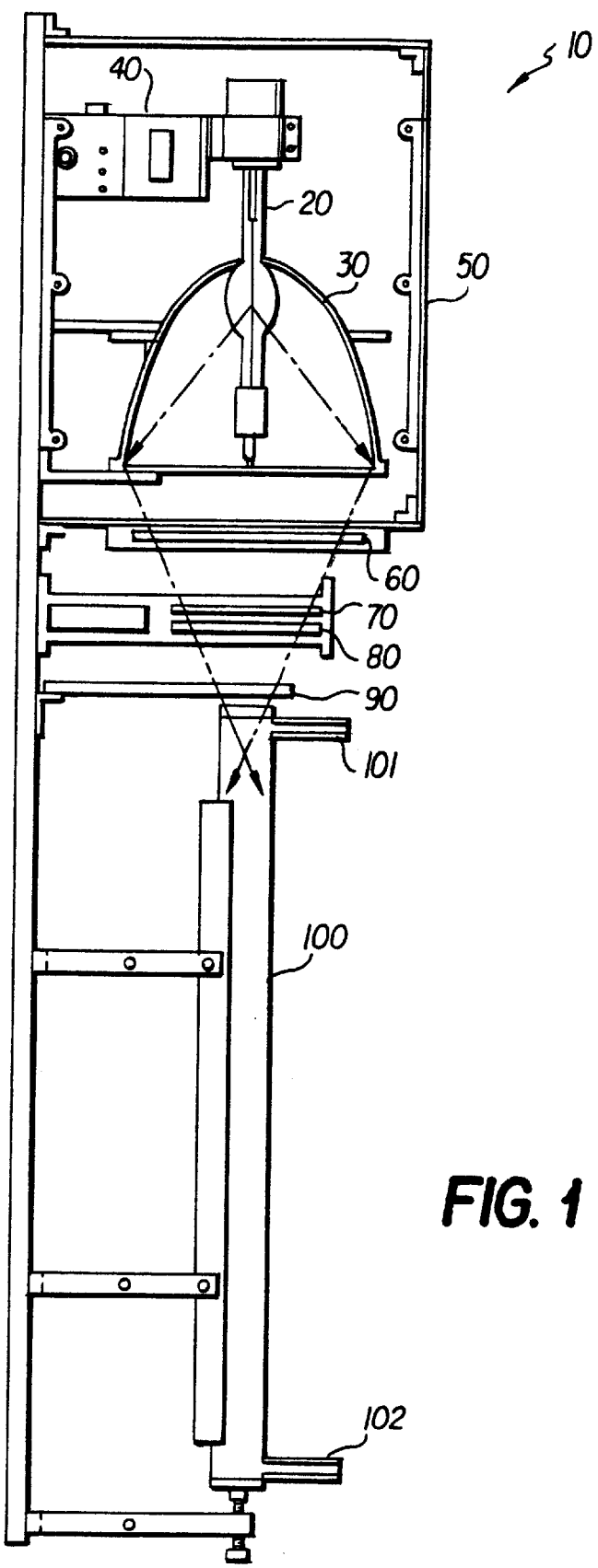
FIG. 1 is a plan view of a single-channel photolysis system for measuring a quantity of $NO_2$ in a gas sample according to a first preferred embodiment of the present invention.

Referring to FIG. 1, the system 10 comprises (a) a UV light source 20 for emitting light capable of photolytically dissociating $NO_2$ in the gas sample to NO; (b) a means 40 for positioning the light source; (c) an ellipsoidal reflector 30 for collecting and focusing the light from the light source; (d) an enclosure 50 for enclosing the light source and the ellipsoidal reflector; (e) an optical filter assembly 60, 70, 80 for receiving, filtering, and transmitting the focused light from the ellipsoidal reflector; (f) a shutter 90 capable of blocking the transmission of the filtered light which is transmitted through the optical filter assembly; (g) a sample photolysis cell 100 for containing a volume of the gas sample; (h) a means 101 for controllably introducing the gas sample to the sample photolysis cell, and a means 102 for controllably delivering the gas sample from the sample photolysis cell; (i) a detector (not shown) capable of detecting an amount of the NO present in the gas sample delivered from the sample photolysis cell, and capable of emitting a signal representative of the amount of NO; and (j) a means (not shown) for measuring the signal so as to quantify the amount of NO.

The UV light source 20 is typically a DC short-arc Hg lamp (HBO series, commercially available from Osram-Sylvania, Danvers, Mass.). Optical emission from these lamps is characterized by intense, pressure-broadened atomic lines from Hg overlaid on a much less intense Xe continuum. A small amount of Xe gas is present to facilitate arc ignition, which is accomplished by a relatively low-voltage (1.7 to 2.0 kV) pulse. Operating voltages range from 20 to 60 v DC, depending on the rated wattage. The small amount of Hg, initially present as liquid droplets, is rapidly vaporized, and at operating temperatures it is Hg vapor that contributes most to the total internal lamp pressure and emission spectrum. Arc dimensions depend somewhat on the specific lamp wattage and typically range from 0.4 to 3 mm in length, and 0.2 to 0.6 mm in diameter. These lamps are very nearly point sources from which the output is easily collected and refocused into the sample photolysis cell 100.

UV light source 20 typically has a rated power of from 50 to 1000W. In a more typical embodiment, UV light source 20 has a rated power of from 100 to 300 W, and even more typically, a rated power of 200 W.

In another embodiment, UV light source 20 could be an Hg-halide lamp.

UV light source 20 is held in a means 40 for positioning the light source, such as, for example, being held vertically by one electrode in a 3-axis positioning stage (Opto-Sigma, Santa Ana, Calif.). This arrangement ensures that the brightest point of the arc can be positioned at the primary focus of ellipsoidal reflector 30. A wide variety of electroformed nickel ellipsoids are available commercially (e.g., Opti-Forms, Temecula, Calif.). An f/1.17 ellipsoid, coated with a thin layer of aluminum for UV reflectance and overcoated with quartz to protect the mirror surface, collects and focuses nearly 80% of the lamp output in a relatively short focal length. When the lamp is properly positioned, an intensely bright spot ~1.0 cm in diameter is obtained at the secondary focus of the ellipsoid.

The UV light source 20, means 40 for positioning the light source, and ellipsoidal reflector 30 are contained inside a small enclosure 50 for both measurement stability and safety reasons. Hg arc lamp UV output stability can be degraded by non-uniform air flow over the lamp, due to variations in Hg vapor pressure induced by fluctuations in the local temperature of the quartz envelope. Enclosure 50 serves to isolate steady airflow due to convection around the lamp from the more turbulent forced-air cooling in the photolysis system. At normal operating temperatures, the internal pressure of arc lamps can be quite high, around 70 bar; the enclosure protects other components of the photolysis system and the operator in the unlikely event of catastrophic lamp failure.

The optical filter assembly comprises a first filter 60, a second filter 70, and a third filter 80, all of which are disposed between the lamp and the sample cell. The optical filters are used to transmit only those wavelengths (DeMore et al., 1997) which photolyze $NO_2$ to produce NO.

First filter 60 is a window, typically of glass construction, such as, for example, Pyrex, which serves to absorb long-wavelength IR radiation, thereby minimizing sample heating and potential interferences from thermal conversion of ambient peroxyacyl nitrate compounds (e.g., peroxyacetyl nitrate (PAN)) and $N_2O_5$.

Second filter 70 is a bandpass filter (such as a BG-3 or UG-5 filter, both available from Schott Glass Technologies, Duryea, Pa.) which absorbs in the visible and mid-IR radiation. This bandpass filter is typically only used with the 50W or 100W Hg lamps, as higher-wattage lamps will degrade the filter over time.

Third filter 80 is a long-pass filter (such as a WG-345 filter from Schott) used to discriminate against other NOy species ($HNO_3$, $HO_2NO_2$, $N_2O_5$, etc.) characterized by increasingly large absorption cross-sections, typically below 345 nm. In another embodiment, however, third filter 80 can comprise large absorption cross-sections below 335 nm, and in still another embodiment, can comprise large absorption cross-sections below 320 nm. While use of the three-filter assembly results in the loss of ~35% of useful lamp output, this is advantageously compensated for by greatly increased selectivity for $NO_2$.

Figure 4:
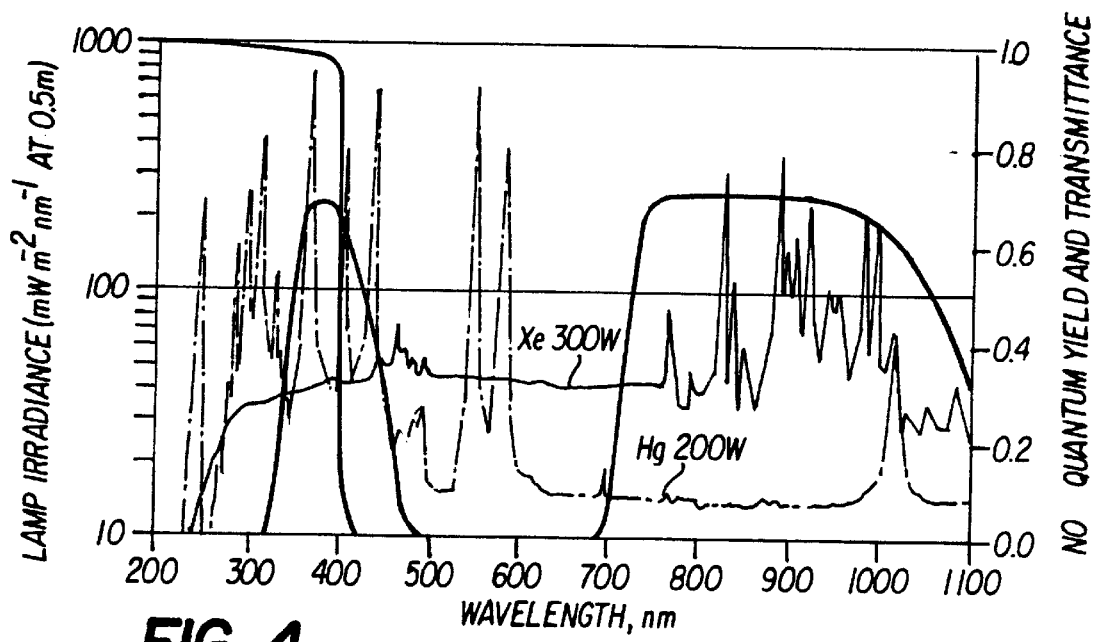
FIG. 4 is a depiction of irradiance data presented as a function of wavelength for 200W Hg and 300W Xe arc lamps.

FIG. 4 is a depiction of irradiance data presented as a function of wavelength for 200W Hg and 300W Xe arc lamps. Hg lamp irradiance data, filter set transmission efficiency, and quantum yields for $NO_2$ photolysis are depicted as a function of wavelength. The shaded region depicts useful wavelengths for photolysis and encompasses the range between 350 nm (50% transmission by the three-filter set) and 402 nm (50% quantum yield for photolysis). $NO_2$ photolysis by Hg lamps is accomplished by three intense atomic emission lines which are pressure-broadened into a single peak centered at ~365 nm. Roughly 14W, or 7% of total Hg lamp output occurs in the 320 to 400 nm wavelength range. Xe lamp irradiance data are shown for comparison and are characterized by significantly lower UV output per watt of power dissipated. Thus, an unfiltered 200W Hg lamp provides a 5-fold increase in useful UV irradiance and a 4-fold decrease in undesirable IR irradiance compared to an unfiltered 300W Xe lamp.

When a separate channel is used to continuously measure ambient NO (i.e., the dual-channel embodiment of the present invention), frequent measurements of NO in the $NO_2$ channel are mandatory to assure accurate $NO_2$ retrieval by difference. Therefore, shutter 90 is located between the filter assembly 60, 70, 80, and sample photolysis cell 100; when the shutter is closed, the cell is darkened and ambient NO can be measured directly. Shutter 90 is typically opaque, or in another more specific embodiment, can be opaque only to wavelengths of radiation below which $NO_2$ is photolytically dissociated to NO.

In one embodiment of the system, a pivoting 0.32-cm thick aluminum shutter is actuated by a pneumatic air cylinder (Bimba Manufacturing, Monee, Ill.). In this embodiment, within a span of 5 seconds, the shutter can be closed, an NO measurement made, and the instrument returned to measuring $NO_2$. Given the relatively low IR output of the lamp, the IR filters, and the short shutter actuation times in this system, undesirable changes in photolysis cell temperature (Gao et al., 1994) are negligible when the shutter is closed.

During operation of the system, sample gas is drawn at reduced pressure through sample photolysis cell 100. The sample photolysis cell can comprise materials of construction selected from the group consisting of quartz, glass, and metal with quartz or glass. In a typical embodiment, the sample photolysis cell is cylindrical in shape, with an inside diameter of 1.5 cm and a length of 20 cm, and is of quartz construction. Quartz provides negligible wavelength filtering beyond that afforded by the filter assembly. The sample photolysis cell is positioned along the z-axis of ellipsoid reflector 30 so that the converging cone of light approximately fills the entrance face, is focused to a point just inside the cell, and diverges thereafter. Outer cell surfaces and the opposite face are typically coated with UV-reflective material to afford maximum illumination along the length of the cell. Aluminum foil works well, but more durable vacuum-deposited coatings are also available.

Means 101 for controllably introducing the gas sample to the sample photolysis cell, sample photolysis cell 100, and means 102 for controllably delivering the gas sample from the sample photolysis cell, each comprises a volume which minimizes the residence time of the gas sample in the system.

The means for detecting the amount of NO is capable of utilizing ozone-induced chemiluminescence or laser-induced fluorescence to effect the detection.

The invention further relates to a method of measuring a quantity of $NO_2$ in a gas sample with the aforementioned single-channel photolysis system 10. In a typical embodiment, the method comprises the steps of (a) introducing a first portion of the gas sample to the sample photolysis cell 100; (b) irradiating the first portion of the gas sample with the light capable of photolytically dissociating $NO_2$; (c) delivering the first portion of the gas sample from the sample photolysis cell to the detector so as to detect the amount of NO (comprising ambient NO and that NO formed by photolysis of ambient $NO_2$) present in the first portion of the gas sample, and so as to emit the signal representative of the first portion amount of NO; (d) measuring the signal so as to quantify the first portion amount of NO; (e) positioning the shutter 90 so as to block the transmission of the filtered light to the sample photolysis cell 100; (f) introducing a second portion of the gas sample to the sample photolysis cell 100; (g) delivering the second portion of the gas sample from the sample photolysis cell to the detector so as to detect the amount of NO present in the second portion of the gas sample, and so as to emit the signal representative of the second portion amount of NO; (h) measuring the signal so as to quantify the second portion amount of NO; and (i) positioning the shutter 90 so as to allow the transmission of the filtered light to the sample photolysis cell 100.

In the method of measuring with the single-channel photolysis system, steps (a) through (i) can be repeated one or a plurality of times, depending upon the particular application.

As indicated above in the description of the single-channel photolysis system, the means 101 for controllably introducing the gas sample to the sample photolysis cell, the sample photolysis cell 100, and the means 102 for controllably delivering the gas sample from the sample photolysis cell, each comprises a volume which minimizes the residence time of the gas sample in the system.

Furthermore, in the method of measuring with the single-channel photolysis system, steps (a) through (i) are performed so as to minimize the gas sample residence time in the system.

The volume of the photolysis cell in the $NO_2$ channel introduces a time lag and acts to smooth ambient concentration variations relative to other channels (Ridley et al., 1994). In previous systems, the raw $NO_2$ signal was carefully adjusted in time to maximize alignment with NO data; thus, $NO_2$ concentrations could only be retrieved on timescales longer than the cell residence time. During periods of large and rapidly changing NO or $NO_2$ concentrations, even small differences in timing lead to very large uncertainties in retrieved $NO_2$ (Ridley et al., 1994).

Thus, in a second preferred embodiment, the present invention advantageously relates to a dual-channel system for measuring a quantity of $NO_2$. In the dual-channel system, sample residence times are made identical by including a cell, equal in volume to the photolysis cell, in the NO channel flow path (see FIG. 2). This configuration permits simple and accurate retrieval of ambient $NO_2$ at high time resolution. While the NO channel time response is degraded relative to that obtained with no added volume, the degradation is minimal in the present design.

Figure 2:
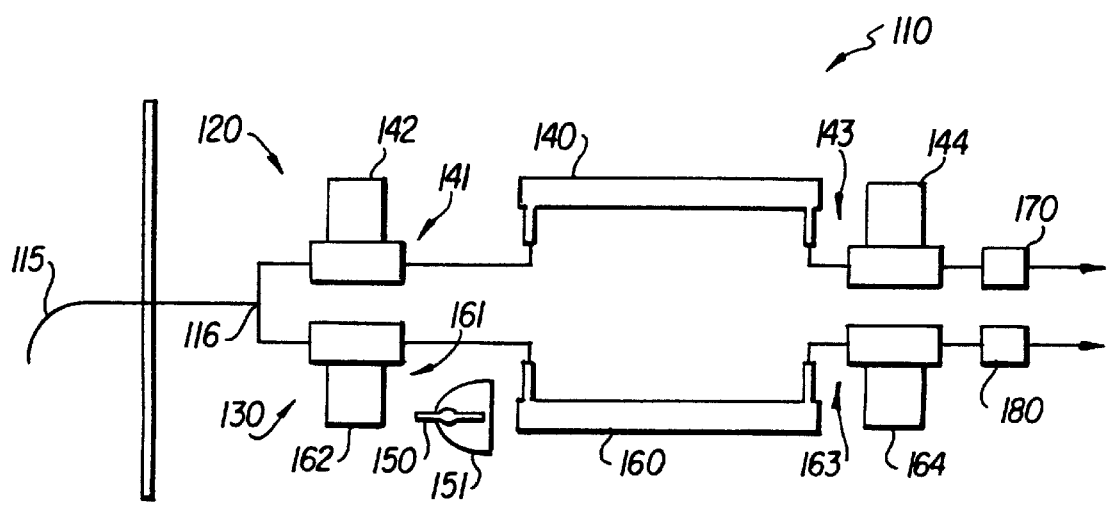
FIG. 2 is a schematic diagram of a dual-channel system for measuring a quantity of $NO_2$ according to a second preferred embodiment of the present invention.

Referring to FIG. 2, the dual-channel photolysis system 110 comprises a gas inlet line 115 for receiving a total gas sample; a flow divider 116 for dividing the total gas sample into a first gas sample having a first gas sample volume, and a second gas sample having a second gas sample volume, the first gas sample volume and the second gas sample volume being minimal and equal; a first channel 120 for detecting ambient NO in the first gas sample; and a second channel 130 for detecting both ambient NO, and NO resulting from the photolytic dissociation of $NO_2$ to NO, in the second gas sample.

In the dual-channel system 110, the first channel 120 comprises (a) an opaque sample cell 140; (b) a first channel means 141 for controllably introducing the first gas sample to the opaque sample cell, and a first channel means 143 for controllably delivering the first gas sample from the opaque sample cell; (c) a first channel detector 170 capable of detecting an amount of NO present in the first gas sample delivered from the opaque sample cell, and capable of emitting a signal representative of the amount of NO in the first gas sample; and (d) a first channel means (not shown) for measuring the signal so as to quantify the amount of NO in the first gas sample.

In the dual-channel system, the second channel 130 comprises (e) a UV light source 150 for emitting light capable of photolytically dissociating $NO_2$ in the second gas sample to NO; (f) a means for positioning the light source; (g) an ellipsoidal reflector 151 for collecting and focusing the light from the light source; (h) an enclosure for enclosing the light source and the ellipsoidal reflector; (i) an optical filter assembly for receiving, filtering, and transmitting the focused light from the ellipsoidal reflector; (j) a shutter capable of blocking the transmission of the filtered light which is transmitted through the optical filter assembly; (k) a sample photolysis cell 160 for containing a volume of the second gas sample; (l) a second channel means 161 for controllably introducing the second gas sample to the sample photolysis cell, and a second channel means 163 for controllably delivering the second gas sample from the sample photolysis cell; (m) a second channel detector 180 capable of detecting an amount of NO present in the second gas sample delivered from the sample photolysis cell, and capable of emitting a signal representative of the amount of NO in the second gas sample; and (n) a second channel means (not shown) for measuring the signal so as to quantify the amount of NO in the second gas sample.

In the dual-channel system, the first channel means 141 for controllably introducing the gas sample, the opaque sample cell 140, the first channel means 143 for controllably delivering the gas sample, and the first channel detector 170 capable of detecting an amount of NO define a first channel gas flow volume. The second channel means 161 for controllably introducing the gas sample, the sample photolysis cell 160, the second channel means 163 for controllably delivering the gas sample, and the second channel detector 180 capable of detecting an amount of NO define a second channel gas flow volume. The first channel gas flow volume, and the second channel gas flow volume, are minimal and equal.

In a typical embodiment, pressure controllers 142 and 162 (Model 640, MKS, Andover, Mass.) upstream of the cells, and mass flow controllers 144 and 164 (Model 1179, MKS) downstream, are used to maintain cell residence times independent of changes in ambient pressure, such as, for example, when the system is airborne. For example, cell pressures of 250 Torr and sample flows of 780 standard cubic centimeters per minute (sccm) afford cell residence times, assuming plug flow, of 0.82 s for a 35 $cm^3$ sample cell volume. Total sample residence times from inlet to detector are 1.41 s at sea level and decrease to 1.25 s at 7600 m altitude. Short residence times greatly minimize reactions with ambient oxidants during sampling (Ridley et al., 1988); nonetheless, these effects are accounted for in NO and $NO_2$ data reduction, as described below.

The system 110 is of relatively simple design, as bypass valves and associated fittings and tubing are not required due to the reduced volume of the photolysis cell. In a typical embodiment, the entire photolysis system, including lamp power supply, optical bench, and shutter pneumatics, is relatively small (60×25×15 cm) and weighs less than 8 kg.

The invention further relates to a method of measuring a quantity of $NO_2$ in a gas sample with the aforementioned dual-channel photolysis system 110. In a typical embodiment, the method comprises the steps of, in the first channel 120, (a) introducing the first gas sample to the opaque sample cell 140; (b) delivering the first gas sample from the opaque sample cell 140 to the first channel detector 170 so as to detect the amount of NO present in the first gas sample, and so as to emit the signal representative of the amount of NO in the first gas sample; and (c) measuring the signal so as to quantify the amount of NO in the first gas sample.

In the second channel 130, the method comprises the steps of (d) introducing a first portion of the second gas sample to the sample photolysis cell 160; (e) irradiating the first portion of the second gas sample with the light capable of photolytically dissociating $NO_2$; (f) delivering the first portion of the second gas sample from the sample photolysis cell 160 to the second channel detector 180 so as to detect the amount of NO (comprising ambient NO and that NO formed by photolysis of ambient $NO_2$) present in the first portion of the second gas sample, and so as to emit the signal representative of the first portion amount of NO; (g) measuring the signal so as to quantify the first portion amount of NO; (h) positioning the shutter 90 (FIG. 1) so as to block the transmission of the filtered light to the sample photolysis cell; (i) introducing a second portion of the second gas sample to the sample photolysis cell 160; (j) delivering the second portion of the second gas sample from the sample photolysis cell 160 to the second channel detector 180 so as to detect the amount of NO present in the second portion of the second gas sample, and so as to emit the signal representative of the second portion amount of NO; (k) measuring the signal so as to quantify the second portion amount of NO; and (l) positioning the shutter 90 so as to allow the transmission of the filtered light to the sample photolysis cell 160.

In the method of measuring with the dual-channel system, steps (a) through (c) are performed simultaneous with said steps (d) through (l). Steps (a) through (c), and (d) through (l), can be repeated one or a plurality of times, depending upon the particular application. Furthermore, in the method of measuring with the dual-channel photolysis system, steps (a) through (c), and (d) through (l), are performed so as to minimize the gas samples' residence time in the system.

Instrument Characterization

Initial photolytic converter characterization was carried out in clean synthetic air in a laboratory setting. In these experiments, calculated and measured signals from ambient nitrogen-containing compounds other than $NO_2$ were determined, and Hg arc lamp j values were evaluated and compared to that obtained using a standard Xe lamp. Ground-based field measurements were carried out at a site on the Green Mountain Mesa near Boulder, Colo., for further testing of Hg lamp stability and UV-induced artifact in a field setting. During the laboratory and ground-based field experiments, a commercially available water-cooled lamp housing (Oriel Instruments, Stratford, Conn.) was used in the photolytic converter. A more compact air-cooled housing was designed for the aircraft instrument and was deployed with a 100W Hg lamp on the field mission. Data from the aircraft instrument are used to characterize $NO_2$ instrument response times, precision, and accuracy.

Laboratory Data

Interference Tests

Interferences may arise from unwanted conversion of other ambient nitrogen-containing compounds to NO or $NO_2$ in the sample lines and photolysis cell, either by gas-phase photolysis, gasphase thermal decomposition, or surface-mediated processes (Ridley et al., 1988; Parrish et al., 1990; Gao et al., 1994; Bradshaw et al., 1999). Gasphase absorption cross-sections for $NO_2$ and several potential interfering NOy species are provided as a function of wavelength in FIG. 5.

Figure 5:
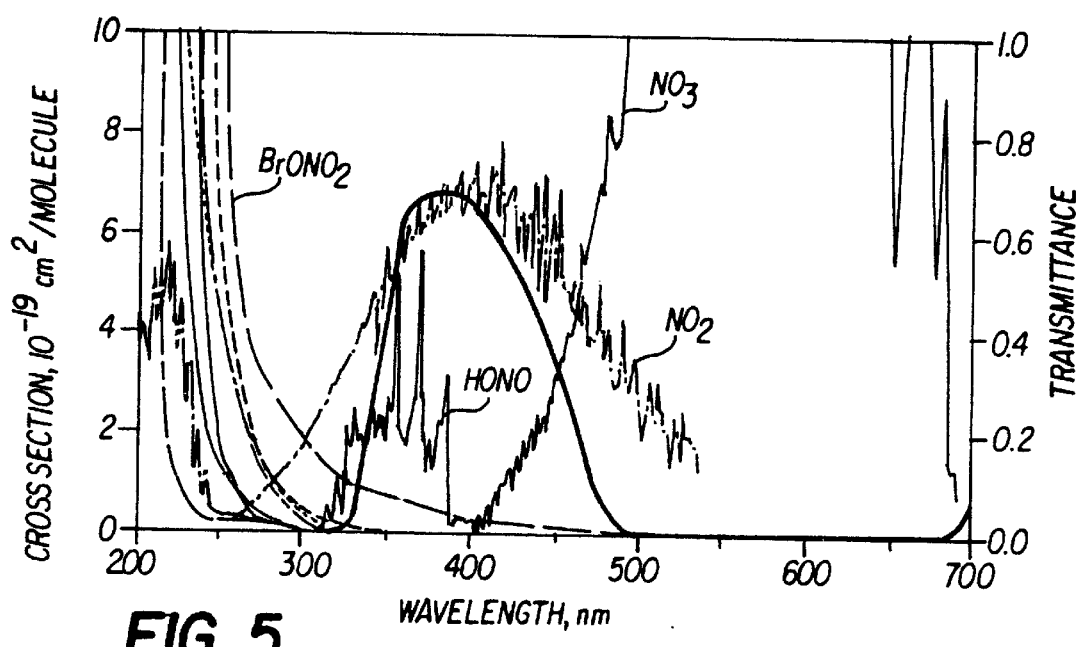
FIG. 5 is a depiction of absorption cross-section data presented as a function of wavelength for $NO_2$ and for potential interferences in a broadband P-CL measurement.

FIG. 5 is a depiction of absorption cross-section data presented as a function of wavelength for $NO_2$ and for potential interferences in a broadband P-CL measurement. No significant interference is calculated from $HNO_3$, PAN, $N_2O_5$, $HO_2NO_2$, $ClONO_2$, and methyl nitrate, due to optical filtering. Optical filtering greatly minimizes interferences from $BrONO_2$, HONO, and $NO_3$.

Relative levels of interference can be calculated from Hg lamp irradiance data, the transmittance of the filter set, and available NOy species absorption cross-section data, and by conservatively assuming quantum yields of 1 for photolysis of these species to detectable products in the gas phase. These calculations represent upper limits and predict an equivalent signal of <0.3% from ambient $ClONO_2$ and $N_2O_5$ and entirely negligible signals from $HNO_3$, $HO_2NO_2$, methyl nitrate, and PAN.

Absorption cross-sections for HONO, $NO_3$, and $BrONO_2$ (FIG. 5) overlap those of $NO_2$ much more strongly and under certain conditions these species may be non-negligible interferences to the $NO_2$ measurement. Assuming quantum yields of 1, ambient HONO will constitute a 37% interference relative to equal concentrations of $NO_2$ (i.e., 1 pptv response from 2.7 pptv HONO); $BrONO_2$ constitutes a 5% interference. When the BG-3 bandpass filter is used, equivalent signal from $NO_3$ is estimated as 10% when wavelength-dependent quantum yields and branching ratios for the two photolysis channels are taken into account (Wayne, R. P., et al., The nitrate radical: physics, chemistry, and the atmosphere, *Atmospheric Environment*, 25A, 1–203, 1991). Without this filter, essentially all $NO_3$ is photolyzed and detected. $BrONO_2$ is only present at low concentrations in the stratosphere. HONO and $NO_3$ are thought to be present at very low concentrations in the atmosphere during the day, and under most night-time conditions $NO_2$ concentrations are much larger than these potential interferences.

Potential interferences due to gas-phase thermal decomposition of PAN, $N_2O_5$, and $HO_2NO_2$ were calculated (DeMore et al., 1997) for total sample residence times of 1.4 s at 303 K appropriate to the present design. While PAN decomposition was calculated to be negligible, roughly 3% of ambient $N_2O_5$ and 12% of ambient $HO_2NO_2$ will thermally decompose to a detectable form during sampling. As with HONO and $NO_3$, ambient concentrations of $N_2O_5$ are expected to be very low during daylight hours, and even after dark this potential interference should be present at low levels relative to concentrations of ambient $NO_2$. Ambient levels of $HO_2NO_2$ are expected to vary significantly with height in the atmosphere, as the lifetime of this species is determined by its thermal equilibrium with $HO_2$ and $NO_2$. Thus, measurements of $NO_2$ by this method in the upper troposphere and lower stratosphere will be most susceptible to interference from $HO_2NO_2$.

Interferences due to surface-induced decomposition of NOy species are difficult to estimate with any confidence. For this reason, conversions of $HNO_3$ and PAN were tested by adding known amounts of these compounds in synthetic air to the instrument in the laboratory. Any signal from these potential interferences represents the sum of gas-phase and surface-mediated processes occurring during sampling. Output from a thermostated permeation tube was used to deliver relatively high concentrations of $HNO_3$ to the $NO_2$ sample line upstream of the pressure controller (FIG. 2). Nylon wool that had been washed in a saturated solution of $NaHCO_3$ was used to remove >99% (Huey, L. G., et al., Fast time response measurements of $HNO_3$ in air with a chemical ionization mass spectrometer, Journal of Geophysical Research, 103, 3355–3360, 1998) of the $HNO_3$ from the calibration stream; it was assumed that in dry zero air the concentrations of NO and $NO_2$, emitted by the permeation source in small amounts, are not affected by passage over the nylon wool. Conversion of $HNO_3$ was estimated by the difference between $NO_2$ channel response obtained by adding 27.2±0.3 pptv $HNO_3$ for 5 minutes to the sample line versus that obtained when the nylon filter was in place. No detectable difference was observed, from which it was estimated that the interference due to $HNO_3$ was less than 0.1% in the present system. This suggests that surface-mediated processes do not contribute significantly to an interference from $HNO_3$ in the instrument as presently configured.

Experiments testing the level of interference due to PAN conversion were carried out using the output of a diffusion source containing a dilute solution of PAN in tridecane (Roberts, J. M., et al., Measurements of PAN, PPN, and MPAN made during the 1994 and 1995 Nashville Intensives of the Southern Oxidant Study: Implications for regional ozone production from biogenic hydrocarbons, *Journal of Geophysical Research*, 103, 22, 473–22, 490, 1998). Injection of the source output onto a 0.53 mm i.d., 15-m long chromatographic column coated with 1-$\mu$m thick RTX-200 provided a PAN sample free of trace impurities, including $NO_2$, prior to sampling into the photolytic converter. Ratios of PAN concentrations measured in the NOy channel to the signal detected in the $NO_2$ channel during the elution of the PAN peak were very steady and represent a conversion fraction of 0.0058±0.0002, or an equivalent signal of 6 pptv $NO_2$ per pptv PAN. This test includes the contributions by gas-phase photolysis, gas-phase thermal decomposition, and surface-induced decomposition of PAN throughout the $NO_2$ system including the illuminated surfaces of the photolysis cell. It is assumed that all of the signal in the $NO_2$ channel in this test was due to PAN decomposition in the photolysis system. Because other tests suggest that PAN decomposition to produce $NO_2$ occurred during chromatographic separation, actual interference from ambient PAN in this system is likely to be somewhat lower.

To summarize, no significant differences in interferences due to gas-phase photolysis were calculated between optically filtered Hg and optically filtered metal-halide systems. A Xe lamp system with a dielectric mirror will be subject to much larger photolytic interferences from $NO_3$ and HONO due to the larger wavelength range admitted into the cell. Gas-phase thermal decomposition is more likely in metal-halide or Xe lamp systems owing to higher wattage levels, and for the Xe system a higher percentage of IR output per watt, of these lamps. Measured interferences from $HNO_3$ and PAN are essentially negligible in the present system.

reflectors, optical filters and cell geometries appropriate to the specific lamp being tested, to provide a realistic measure of conversion attained in photolytic systems optimized for each lamp.

All cells were wrapped with aluminum foil to maximize sample irradiation for each experiment. Other factors, such as level of interferences, thermal management issues, instrument time response, simplicity of data reduction, and lamp stability and longevity, are equally important in an operational system but were not addressed in these particular tests.

Relevant information for each experiment is provided in Table 1. Cell residence times were calculated assuming plug flow and were varied by adjusting the photolysis cell pressure while maintaining a constant mass flow through the cell. Known amounts of $NO_2$ (ca. 1 pptv) were generated by controlled addition of ozone to a calibrated standard of NO in nitrogen.

Figure 3:
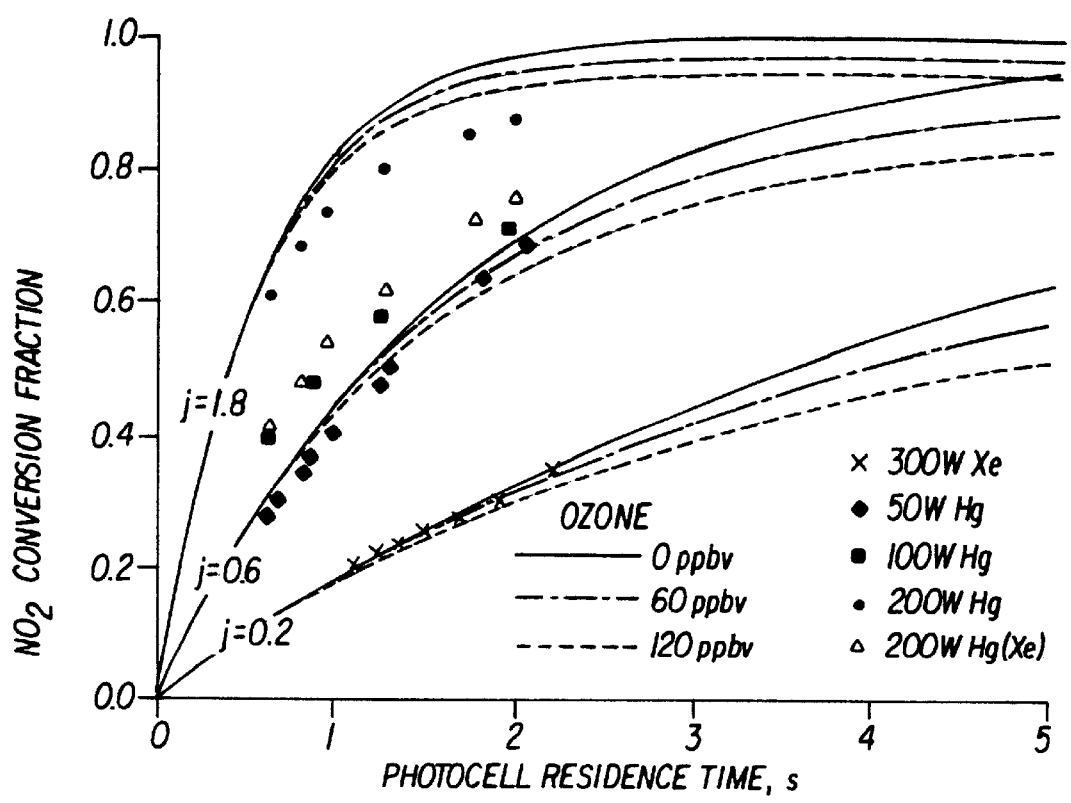
FIG. 3 is a depiction of $NO_2$ conversion fractions, both measured and calculated using Equation (4) for different j values and ambient oxidant levels, plotted as a function of photolysis cell residence time.

FIG. 3 is a depiction of $NO_2$ conversion fractions, both measured and calculated using Equation (4) for different j values and ambient oxidant levels, plotted as a function of photolysis cell residence time. Measured CF data are plotted as a function of photolysis cell residence time to provide an estimate of the effective j value for each lamp/reflector/cell combination. Theoretical curves for a range of j values are calculated according to Equation (4) and are plotted for comparison.

The focused Hg lamps are shown to be significantly more efficient per watt of total power dissipated than the ER-2 metal-halide lamp, the Hg(Xe), or the collimated Xe lamps used in conventional photolysis systems. While the 400W metal-halide lamp emits more UV light (65W between 320 and 400 nm, compared to 14W by the 200W Hg), it is theorized that the higher effective j value provided by the 200W Hg lamp is largely due to increased efficiency in collecting and focusing light from a point versus a line source.

TABLE 1

Experimental Parameters and Results of Lamp Comparison Tests

| Rated Power & Lamp Type | 50 W Hg | 100 W Hg | 200 W Hg | 200 W Hg(Xe) | 300 W Xe | 400 W Metal halide |
|---|---|---|---|---|---|---|
| Measured Power | 53 W | 97 W | 224 W | 225 W | — | — |
| Arc shape | Point | Point | Point | Point | Point | Line |
| Reflector | External ellipsoidal | External ellipsoidal | External ellipsoidal | External ellipsoidal | Internal parabolic | External parabolic |
| Beam shape | Focused | Focused | Focused | Focused | Collimated | Collimated |
| Optical filter set | Pyrex/BG-3/WG-345 | Pyrex/BG-3/WG-345 | Pyrex/WG-345 | Pyrex/WG-345 | UV ("cold") mirror | Pyrex/UG-5/WG-345 |
| Cell dimensions (i.d. × length) | 1.5 × 20 cm | 1.5 × 20 cm | 1.5 × 20 cm | 1.5 × 20 cm | 2.5 × 10 cm | 5 × 25 cm |
| Sample air temperature | 24° C. | 24° C. | 40° C. | 36° C. | 45° C. | — |
| Effective j value | 0.54 s$^{-1}$ | 0.73 s$^{-1}$ | 1.4 s$^{-1}$ | 0.79 s$^{-1}$ | 0.20 s$^{-1}$ | 0.75 s$^{-1}$ |

Lamp Comparison Tests $NO_2$ conversion fractions were determined in clean synthetic air using a variety of lamps. The specific combination of lamp, reflector, optical filter set, photolysis cell geometry, and sample residence time determines the instrumental sensitivity to $NO_2$ afforded by a given converter system. Therefore, the following experiments were performed with In the data illustrated in Table 1, the sample air temperatures are measured at the exit of the uncooled cell, so as to provide a relative measure of system IR irradiances.

Some ionically colored filter glasses, such as the Schott BG and UG glasses, are subject to solarization and transmission loss when exposed to intense UV light (e.g., Del Negro et al., 1999). While use of the 50W Hg lamp induces minimal transmission degradation over time, direct exposure of the BG-3 filter to 200W Hg lamp output causes permanent reductions of up to 50% in transmission at 365 nm after only 30 minutes of exposure. As focused 200W Hg lamps seem to preclude the use of ionically colored glass, an option to the use of these filters would be changing to a two-filter set of Pyrex and WG-345 alone.

Thus in another embodiment, either the single-channel or the dual channel photolysis system can comprise an optical filter assembly which comprises a first filter and second filter. The first filter is a window capable of absorbing long-wavelength infrared radiation, and the second filter is a long-pass filter comprising large absorption cross-sections below 345 nm, or below 335 nm, or below 320 nm.

Removal of the BG-3 filter would increase the interference from gas-phase $NO_3$ to unity, and would serve to increase sample heating by roughly 10° C. without active cell cooling. The data for the 200W lamps in FIG. 3 and Table 1 were taken without the BG-3 filter. All other reported data, including ambient measurements, were taken using 50W and 100W lamps with the full three-filter set described above.

Ground-based Field Data

Artifact Levels

Residual, or UV-induced artifact, signals in P-CL systems obtained when sampling $NO_2$-free air are regularly observed and, if large, can severely degrade the accuracy of $NO_2$ measurement at trace levels (Kley et al., 1980; Parrish et al., 1990; Gao et al., 1994; Ridley et al., 1994; Ridley, B., et al., Is the Arctic surface layer a source and sink of $NO_x$ in Winter/Spring?, *Journal of Atmospheric Chemistry*, 36, 1–22, 2000). UV-induced artifact signal is attributed to release of NOx from surface contaminants when the photolysis cell is illuminated. Freshly cleaned cells typically produce negligible artifact levels, which then increase over time when ambient air is sampled; physically filtering the sample upstream of the converter has been shown to decrease artifact signal and slow the rate of increase (Parrish et al., 1990; Gao et al., 1994). Some converter designs attempt to minimize direct illumination of the photolysis cell walls in an effort to reduce artifact signal (Ridley et al., 1988; Wang, T., et al., Ground-based measurements of NOx and total reactive oxidized nitrogen (NOy) at Sable Island, Nova Scotia, during the NARE 1993 summer intensive, *Journal of Geophysical Research*, 101, 28, 991–29, 004, 1996; Ridley et al., 2000).

The present system provides direct and intense surface illumination as light diverges past the focal point and undergoes multiple reflections from the cell walls (see configuration in FIG. 1). To characterize UV-induced artifacts in this system, ambient air was sampled continuously for a week to permit surface contamination to accumulate in the photolysis cell. During this experiment, extended periods of upslope flow conditions were sampled. Upslope flow provides an opportunity to mix fresh emissions from a metropolitan area with air recently affected by strong sources of ammonia from cattle and pig feed lot operations; under these conditions, the transport of high levels of gas-phase nitric acid and ammonium nitrate aerosol to the site was likely (Fehsenfeld et al., 1998). These conditions were exploited to study the buildup of UV-induced artifact in the photolysis system under conditions relevant to the polluted troposphere.

No additional physical sample filtering was employed, and the cell was not cleaned for the duration of these tests. Resulting artifact signal was measured daily in the evenings by overflowing the system with zero air for 10 minutes. Initial artifact for the clean cell was 15 pptv equivalent $NO_2$, increasing approximately linearly over time to 81 pptv after 5 days of continuous sampling. When the WG-345 long-pass optical filter was removed from the light path, the artifact signal immediately increased to several hundred pptv and promptly returned to 85 pptv when the filter was replaced. Subsequent cleaning of the cell by briefly rinsing with distilled water reduced the artifact to less than 10 pptv.

These findings implicate a highly water-soluble nitrogen-containing compound characterized by increasingly large absorption cross-section below 350 nm. Ambient $HNO_3$ is a likely candidate, in agreement with findings reported by Parrish et al. (1990) and Gao et al. (1994), which suggested involvement of aerosol $HNO_3$. Thus, UV-induced artifact is greatly reduced by the use of optical filters in the focused Hg lamp system, increases slowly over time, and is easily kept below 15 pptv by daily cleaning of the photolysis cell with distilled water. Physically filtering the sample air to remove aerosol (Parrish et al., 1990) and actively cooling the cell below present air-cooled operating temperatures of 303 K (Ridley et al., 1988; Ridley et al., 2000) is likely to further reduce the artifact to below detectable levels.

Lamp Stability

Different timescales for lamp stability may be defined in different ways. For example, lamp flicker occurring on short, 1- to 5-s timescales, will decrease the precision of the $NO_2$ data but may be compensated for by data averaging. Lamp wander may occur on timescales on the order of the calibration cycle and will result in measurement inaccuracy due to a time-varying bias in the derived instrumental sensitivity for $NO_2$. Lamp drift (typically, decrease in output due to physical degradation of lamp components) occurring on timescales longer than the calibration cycle will determine the useful life of a given lamp. Conventional Xe lamp systems are fairly well characterized in terms of flicker, wander, and drift; equivalent information on Hg lamps used for $NO_2$ photolysis was desired.

Hg arc lamp flicker and wander were evaluated by continuously sampling a known amount of $NO_2$ in zero air into the system. $NO_2$ data taken at 1 Hz showed the expected Poisson distribution exhibited by the instrument when measuring NO, and no longer-term variation on scales of seconds to minutes was noted over the course of the hour-long test.

Lamp wander was further evaluated by monitoring derived conversion fractions for $NO_2$ over time during a field experiment. When low and constant ambient levels of $NO_2$ were transported to the site by steady westerly winds (Fehsenfeld et al., 1998), conversion fractions determined in 12 standard addition calibrations to ambient air varied less than 5% over the course of 48 hours of continuous operation of a 50W Hg lamp. The 100W Hg lamp tested exhibited a CF=0.402±0.018 (14 standard addition calibrations) over a 20-hour period, demonstrating a stability of better than ±4%. During the 100W lamp test, some of the fluctuation about the average CF was due to ambient variability occurring during the 2-minute-long calibration cycles.

Thus, flicker and wander in Hg arc lamps are shown to be sufficiently small that normal instrumental calibration cycles can provide precise and accurate $NO_2$ measurements in a field setting.

Hg lamp drift on longer timescales is as yet uncharacterized, as data obtained thus far are not sufficient to evaluate manufacturer claims of 200 hrs (50W Hg), 400 hrs (100W Hg), and 1000 hrs (200W Hg) for average lamp lifetimes. For comparison, the stated lifetime of a standard 300W Xe lamp is 1000 hrs. These lifetimes are estimated for continuous operation, and all lamps are subject to increased erosion of the electrodes upon ignition. Hg lamps are characterized by much lower ignition voltages, and are likely to be less prone to electrode degradation with repeated starts. Much of the operational cost in photolytic $NO_2$ systems is associated with regularly scheduled lamp replacement. Assuming that lifetimes are comparable, use of the 200W Hg lamp will result in substantial cost savings over time, as these lamps are available for 25% of the cost of a 300W Xe lamp.

Aircraft-based Field Data

Instrument Time Response and Accuracy

Effects of the added cell volume on NO and $NO_2$ channel response times can be evaluated in two ways, by examining the calibration signal rise time of the $NO_2$ channel and by a comparison of retrieved ambient NO and $NO_2$ data to ambient NOy. Assuming the photocell shutter actuation is instantaneous, the 1/e response time of the $NO_2$ channel to the step function generated upon cell illumination provides a measure of instrument response. This tests the instrument from the photolysis cell to the detector, a volume which accounts for roughly 75% of the total sample residence time. Rise times from 10-Hz data during multiple in-flight $NO_2$ calibration sequences performed during an aircraft mission can be fit with a single-exponential rise time constant of 0.65±0.02 s. The exponential character of $NO_2$ channel response to this step fiction indicates some smoothing of ambient variability is to be expected at timescales of a second or less.

More rigorous instrument challenges are provided by ambient measurements during near-source aircraft transects of plumes from large, coal-fired power plants. Extremely large and rapid changes in ambient NOy species mixing ratios are typically encountered during these transects, with ambient NO varying over orders of magnitude in the span of seconds (Ryerson, T. B., et al., Emissions lifetimes and ozone formation in power plant plumes, *Journal of Geophysical Research*, 103, 22, 569–22, 583, 1998).

These plume transects represent the most extreme spatial and temporal gradients in NO and $NO_2$ likely to be encountered in the ambient atmosphere. At mixing ratios over ~100 pptv in these transects, nearly all of the measured NOy is composed of NO and $NO_2$, to which the NOy channel responds very rapidly. Therefore, the 10-Hz raw data from the NOy channel serves as a reference against which NO and $NO_2$ channel sample lag and smoothing (Ridley et al., 1994) may be evaluated.

Figure 6A:
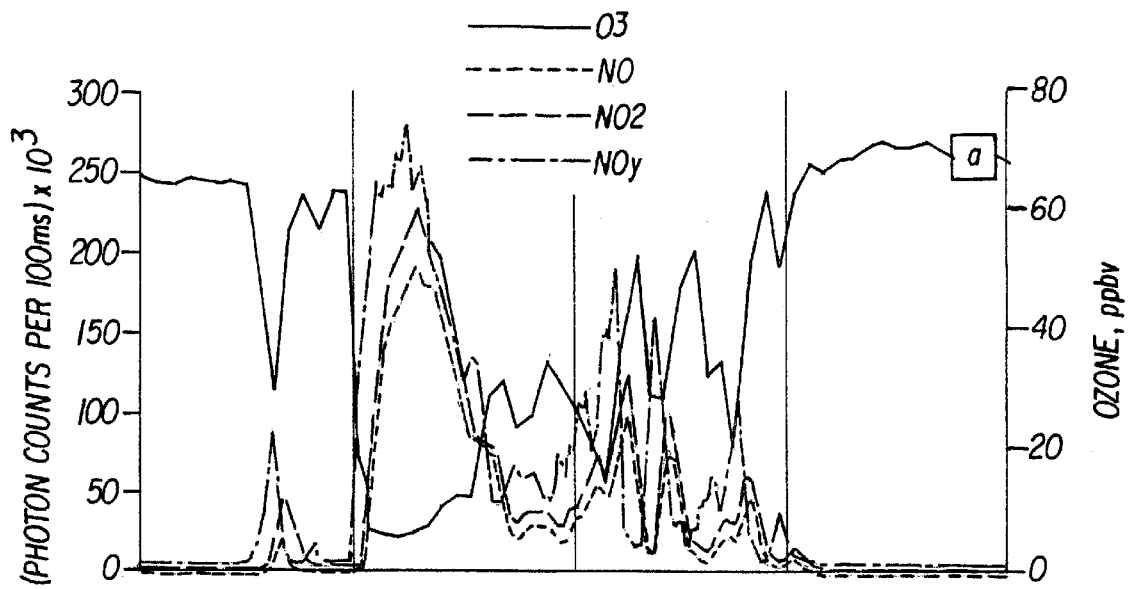
FIG. 6a is a depiction of a time series of NOy instrument photon count rates, in which 10-Hz data are shown for an aircraft transect 11 km downwind of a power plant.

An example of plume transect data is presented in FIG. 6a. FIG. 6a is a depiction of a time series of NOy instrument photon count rates, in which 10-Hz data are shown for a 60-s aircraft transect 11 km downwind of a power plant. The NO and $NO_2$ channels respond identically to ambient variations; a small amount of smoothing and a 0.9-s lag are apparent when compared to the NOy channel response. Ozone mixing ratios measured at 1 Hz are shown.

The 10-Hz NO and $NO_2$ data in FIG. 6a clearly lag the NOy data by ~0.9 s. A lag of 0.7 s relative to NOy is expected at this altitude based solely on the difference in calculated sample residence times between these channels. A small amount of smoothing of ambient variation is also apparent in these 10-Hz data relative to NOy. Smoothing in NO and $NO_2$ induced by the added cell volume is minimal when compared to the measured ozone data along the transect, which are presented in FIG. 6a as 1-s averages. Most significant is that NO and $NO_2$ channels exhibit identical lag and smoothing as a result of matched sample paths, permitting the signal due to ambient NO to be subtracted directly from the total $NO_2$ channel signal.

Previous reports of $NO_2$ measurements during periods of ambient variability have either discarded data (Ryerson et al., 1998) or applied empirically-determined smoothing procedures to the NO data during data reduction (Ridley et al., 1994; Gillani, N. V., et al., Relative production of ozone and nitrates in urban and rural power plant plumes 1. Composite results based on data from 10 field measurement days, *Journal of Geophysical Research*, 103, 22, 593–22, 615, 1998; Tanner, R. L., et al., Measuring inorganic nitrate species with short time resolution from an aircraft platform by dual-channel ozone chemiluminescence, *Journal of Geophysical Research*, 103, 22, 387–22, 395, 1998; Luria, M., et al., The evolution of photochemical smog in a power plant plume, *Atmospheric Environment*, 33, 3023–3036, 1999). Despite the extreme variability shown in FIG. 6a, no time-shifting or smoothing procedures are required for data retrieval from the present system.

Figure 6B:
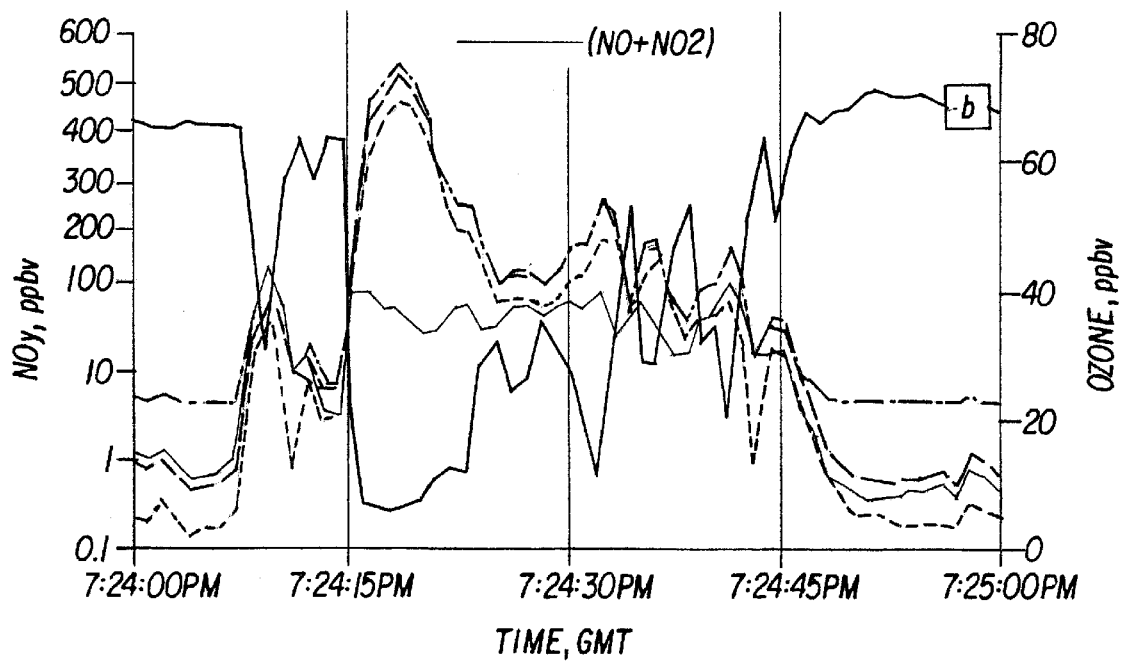

FIG. 6b is a depiction of retrieved mixing ratio data, averaged to 1-s intervals, for the plume transect depicted in FIG. 6a. NO and $NO_2$ data have been advanced 0.9 s to account for sampling lag (i.e., longer sample transit times). The NOy species mixing ratios below 100 pptv are displayed on a log scale to show detail. Accurate recovery of ambient $NO_2$ at high time resolution is demonstrated by agreement between the sum (NO+$NO_2$) and NOy where the total mixing ratio exceeds 100 pptv; the differences throughout the transect are less than 5% of the total ambient levels. No spurious variation in derived $NO_2$ is apparent either when entering or exiting the plume. Thus, minimizing the photocell volume and matching NO and $NO_2$ flow paths permits retrieval of $NO_2$ mixing ratios on timescales equal to or less than the photocell residence time. The presence of an added volume in the NO channel has not significantly degraded the 1-s averaged mixing ratio data, as demonstrated by low scatter and the high degree of anticorrelation ($r^2>0.990$) with measured ozone during the plume transect.

Comparison with Calculated $NO_2$

Measured $NO_2$ in the continental boundary layer was compared to that calculated from the Leighton relationship, which neglects the effects of ambient peroxy radicals (Leighton, 1961). Ten-second averages of measured NO, $O_3$, temperature, pressure, and $NO_2$ photolysis frequencies (Shetter, R. E., et al., Photolysis frequency measurements using actinic flux spectroradiometry during the PEM-Tropics mission: Instrumentation description and some results, *Journal of Geophysical Research*, 104, 5647–5661, 1999) were used in the calculation. At continental boundary layer concentrations of 0.3 to 0.8 pptv $NO_2$ typically observed, measured and calculated $NO_2$ values agree within ±(40 pptv+7%), well within the combined uncertainties of the measurements. Agreement between these two methods was better than 10% overall at the elevated concentrations encountered in urban and power plant plumes.

$NO_2$ Data Reduction

Published data reduction techniques typically assume pseudo-first order conditions in NO and $NO_2$ (e.g., Bollinger, 1982; Ridley et al., 1988; Parrish et al., 1990). When these conditions are satisfied, an analytical solution to the two coupled differential equations exists, from which changes in the NO, $NO_2$, and ozone stationary state occurring during sampling can be calculated. Under urban and power plant plume conditions in which NO>20 pptv or so, this assumption is no longer strictly valid.

A numerical method was used to evaluate the changes in NO, $NO_2$, and ozone during sampling, similar to a recent report by Pätz and co-workers (Pätz, H.-W., et al., Measurements of trace gases and photolysis frequencies during SLOPE96 and a coarse estimate of the local OH concentration from HNO$_3$ formation, *Journal of Geophysical Research*, 105, 1563–1583, 2000). This requires integration of three coupled equations (Leighton, 1961) over the sample residence time from inlet tip to detector, under appropriate conditions of temperature and pressure for each section of sampling line. Under all conditions sampled by aircraft in the field mission, this correction to the NO and NO$_2$ concentrations averaged 2–3%, and was never larger than 6%. This numerical method compared very well to results for NO and NO$_2$ obtained analytically under the simpler (and computationally quicker) pseudo-first order assumption.

Residence times in the present system of less than two seconds, from inlet tip to detector, greatly facilitate simple and accurate retrieval of ambient NO, NO$_2$, and ozone, and are highly desirable for aircraft measurements. However, short residence times have not always been a design criterion for ground-based measurement systems. For example, the current maximum sampling residence time recommended by the Environmental Protection Agency is 20 seconds. In typical urban and suburban areas, relatively large changes may occur to concentrations of these coupled species during a 20-s sampling interval. Whenever possible, however, sampling times should be minimized to increase confidence in measured NO, NO$_2$, and ozone data (Ridley et al., 1988).

The various embodiments of the present invention, therefore, provide a system and a method for measuring a quantity of NO$_2$ in a gas sample.

The advantages associated with the embodiments of the present system and method are numerous. Generally, the invention facilitates more efficient, more specific, and simpler NO$_2$ detection, with significantly improved time response, as compared to previous P-CL designs.

First, the system enables the use of a short-arc high-pressure Hg lamp. This provides approximately a factor of 5 increase in UV output, and a factor of 4 decrease in undesired IR output, per watt of power dissipated relative to a standard Xe lamp. Increased efficiency permits significantly enhanced sensitivity, increased time resolution, and minimizes sample heating. As most of the useful power from the Hg lamp comes in a relatively narrow band of wavelengths centered around 365 nm, optical filtering provides increased specificity for NO$_2$ without undue reduction of conversion efficiency. In addition, the point-source character of the Hg lamps permits efficient collection of the emitted light.

Secondly, the system provides for focusing the lamp output. Enhanced efficiency is attained by focusing lamp output into the sample photolysis cell, thereby significantly increasing the photon flux (j value in Equation 4). This improves upon previous photolytic converter systems in which lamp output is collimated.

Thirdly, the system uses an ellipsoidal mirror external to the lamp. Locating the Hg lamp arc at one focus of a fast (i.e., f/2 or better) external ellipsoidal mirror collects nearly 80% of total emitted light. For comparison, a laboratory mirror and lens system using the same lamp collects only about 10–20% of the lamp output. The external ellipsoidal mirror is not subject to optical surface degradation from sputtered electrode material during lamp ignition and operation, is much less subject to distortion at typical operating temperatures, and permits easy realignment of the arc at the mirror focus. None of these advantages is afforded by the Xe lamps used in the conventional NO$_2$ photolysis converters, which are characterized by internal parabolic reflectors integrated with the discharge electrodes.

Fourthly, the system changes the aspect ratio of the sample cell so as to increase time response. Use of a relatively narrow and long sample cell minimizes longitudinal diffusion during sample transit, preserving high-frequency variations in ambient NO$_2$. Previous sample cell designs are matched to physically larger lamps and spot sizes, are characterized by larger diameter-to-length ratios, and result in more complete attenuation of high-frequency data.

Finally, the dual-channel embodiment of the system matches NO and NO$_2$ sample flow paths in a two-channel instrument. Matching sample paths permits greatly simplified data reduction procedures, and significantly enhances the time resolution attained by the NO$_2$ measurement. For the first time, NO$_2$ measurements by P-CL can be obtained on timescales equal to or faster than the sample cell residence time. Improved time resolution, at 1 second or better, in the present system extends the measurement of NO$_2$ to new areas, such as studying turbulent fluxes of NO$_2$ and quantifying ambient concentrations in power plant emission plumes. Previous measurements made with conventional devices could only retrieve data on timescales longer than the sample cell residence time, and were subject to large uncertainties under conditions of high atmospheric variability.

The applications of the photolytic system are varied and numerous. The system can be used, in conjunction with an NO detector, as a specific measurement of gas-phase NO$_2$ at concentrations ranging from parts per trillion to parts per million or higher. Current uses involve ambient atmospheric air measurements for research or regulatory purposes, the study of gas-phase reaction kinetics in a laboratory setting, and a wide variety of industrial process monitoring applications. A variety of potential future medical applications might involve the non-invasive monitoring of human breath for NO$_2$.

While only certain preferred embodiments of this invention have been shown and described by way of illustration, many modifications will occur to those skilled in the art. For example, while the system has been described in the context of an atmospheric air measurement application, its use is equally applicable to any service in which it would be desirable to have an efficient, lightweight, and relatively inexpensive photolysis system which provides a simple and accurate method for the measurement of NO$_2$.

By way of further example of modifications within the scope of this invention, while the system has been described as employing an Hg lamp of up to 200W rated power as the light source for photolysis, another embodiment could comprise a lamp of even higher power. The choice of lamp rated power is, of course, dependent upon the specific combination of reflector, optical filter set, photolysis cell geometry, sample residence time, and desired instrumental sensitivity to NO$_2$.

For example, higher wattage Hg lamps of up to 1000W rated power are available. A comparison of the tested performance of a 200W lamp to manufacturer irradiance data suggests roughly a 50% increase in total power at 365 nm could be provided by use of a 350W lamp, a factor of two increase by a 500W lamp, and a factor of three by a 1000W lamp.

By way of further example of modifications within the scope of this invention, while the present system employs an air-cooled design, another embodiment could employ active cell cooling to cool the photolysis cell below ambient temperatures in order to decrease spurious (i.e., artifact) signal. In the present air-cooled design, a clean cell at 303

K typically exhibits UV-induced $NO_2$ artifacts at the 10–20 pptv level. For measurements in remote regions or in the free troposphere, however, this constitutes a large uncertainty in derived $NO_2$ mixing ratios.

By way of further example of modifications within the scope of this invention, while the present system employs an Hg lamp to effect photolysis, another embodiment could employ a monochromatic light source. A significant improvement in instrument sensitivity and time response would be afforded by the use of a high-power CW laser. An average laser power of 100 mW at 355 nm could provide a $jNO_2$ value approaching $3.0\ s^{-1}$. At these high j values, the required photolysis cell volume approaches that of an equivalent length of tubing, offering the possibility of >10 Hz instrument response. Interferences due to thermal decomposition or photolysis of other nitrogen-containing compounds should be greatly minimized by the use of a monochromatic light source. A compact solid-state laser, with output either below or above the photodissociation wavelength threshold, could produce significant improvements in $NO_2$ measurements based either on photolysis or on laser-induced fluorescence.

By way of further example of modifications within the scope of this invention, while the dual channel embodiment of the present system employs an inlet line flow divider, another embodiment could comprise a dedicated inlet system for each of the two channels, with both inlet systems designed to produce minimal and equal sample residence times.

By way of further example of modifications within the scope of this invention, while the reflector has been described as being ellipsoidal in shape, another embodiment could comprise a reflector having a different shape, as long as the shape enables the reflector to be a focusing reflector.

It is, therefore, desired that it be understood that it is intended herein to cover all such modifications that fall within the true spirit and scope of this invention.

What is claimed is:

1. A single-channel photolysis system for measuring a quantity of $NO_2$ in a gas sample, said system comprising:
    (a) a UV light source for emitting light capable of photolytically dissociating $NO_2$ in said gas sample to NO;
    (b) a means for positioning said light source;
    (c) a reflector for collecting and focusing said light from the light source;
    (d) an enclosure for enclosing said light source and said reflector;
    (e) an optical filter assembly for receiving, filtering, and transmitting said focused light from the reflector;
    (f) a shutter capable of blocking the transmission of said filtered light which is transmitted through the optical filter assembly;
    (g) a sample photolysis cell for containing a volume of said gas sample;
    (h) a means for controllably introducing said gas sample to said sample photolysis cell, and a means for controllably delivering said gas sample from said sample photolysis cell;
    (i) a detector capable of detecting an amount of said NO present in said gas sample delivered from the sample photolysis cell, and capable of emitting a signal representative of said amount of NO; and
    (j) a means for measuring said signal so as to quantify said amount of NO.

2. A single-channel photolysis system according to claim 1, wherein said UV light source has a rated power of from 50 to 1000 W.

3. A single-channel photolysis system according to claim 1, wherein said UV light source has a rated power of from 100 to 300 W.

4. A single-channel photolysis system according to claim 1, wherein said UV light source has a rated power of 200 W.

5. A single-channel photolysis system according to claim 1, wherein said UV light source is a DC short-arc Hg or Hg-halide lamp.

6. A single-channel photolysis system according to claim 1, wherein said optical filter assembly comprises a first filter, a second filter, and a third filter.

7. A single-channel photolysis system according to claim 6, wherein said first filter is a window capable of absorbing long-wavelength infrared radiation.

8. A single-channel photolysis system according to claim 6, wherein said second filter is a bandpass filter capable of absorbing visible and mid-infrared radiation.

9. A single-channel photolysis system according to claim 6, wherein said third filter is a long-pass filter comprising large absorption cross-sections below 345 nm.

10. A single-channel photolysis system according to claim 6, wherein said third filter is a long-pass filter comprising large absorption cross-sections below 335 nm.

11. A single-channel photolysis system according to claim 6, wherein said third filter is a long-pass filter comprising large absorption cross-sections below 320 nm.

12. A single-channel photolysis system according to claim 1, wherein said optical filter assembly comprises a first filter and second filter.

13. A single-channel photolysis system according to claim 12, wherein said first filter is a window capable of absorbing long-wavelength infrared radiation.

14. A single-channel photolysis system according to claim 12, wherein said second filter is a long-pass filter comprising large absorption cross-sections below 345 nm.

15. A single-channel photolysis system according to claim 1, wherein said shutter is opaque.

16. A single-channel photolysis system according to claim 1, wherein said shutter is opaque only to wavelengths of radiation below which $NO_2$ is photolytically dissociated to NO.

17. A single-channel photolysis system according to claim 1, wherein said sample photolysis cell comprises materials of construction selected from the group consisting of quartz, glass, and metal with quartz or glass.

18. A single-channel photolysis system according to claim 1, wherein said means for controllably introducing the gas sample to the sample photolysis cell, said sample photolysis cell, and said means for controllably delivering the gas sample from the sample photolysis cell, each comprises a volume which minimizes a residence time of the gas sample in the system.

19. A single-channel photolysis system according to claim 1, wherein said means for detecting an amount of NO is capable of utilizing ozone-induced chemiluminescence or laser-induced fluorescence.

20. A single-channel photolysis system according to claim 1, wherein said reflector is ellipsoidal in shape.

21. A dual-channel system for measuring a quantity of $NO_2$, said system comprising;
    a gas inlet line for receiving a total gas sample;
    a flow divider for dividing said total gas sample into a first gas sample having a first gas sample volume, and a second gas sample having a second gas sample volume, said first gas sample volume and said second gas sample volume being equal;
a first channel for detecting ambient NO in said first gas sample; and
a second channel for detecting both ambient NO, and NO resulting from the photolytic dissociation of $NO_2$ to NO, in said second gas sample,
said first channel comprising:
(a) an opaque sample cell;
(b) a first channel means for controllably introducing said first gas sample to said opaque sample cell, and a first channel means for controllably delivering said first gas sample from said opaque sample cell;
(c) a first channel detector capable of detecting an amount of said NO present in the first gas sample delivered from the opaque sample cell, and capable of emitting a signal representative of said amount of NO in the first gas sample; and
(d) a first channel means for measuring said signal so as to quantify said amount of NO in the first gas sample, and
said second channel comprising:
(e) a UV light source for emitting light capable of photolytically dissociating $NO_2$ in said second gas sample to NO;
(f) a means for positioning said light source;
(g) a reflector for collecting and focusing said light from the light source;
(h) an enclosure for enclosing said light source and said reflector;
(i) an optical filter assembly for receiving, filtering, and transmitting said focused light from the reflector;
(j) a shutter capable of blocking the transmission of said filtered light which is transmitted through the optical filter assembly;
(k) a sample photolysis cell for containing a volume of said second gas sample;
(l) a second channel means for controllably introducing said second gas sample to said sample photolysis cell, and a second channel means for controllably delivering said second gas sample from said sample photolysis cell;
(m) a second channel detector capable of detecting an amount of said NO present in said second gas sample delivered from the sample photolysis cell, and capable of emitting a signal representative of said amount of NO in the second gas sample; and
(n) a second channel means for measuring said signal so as to quantify said amount of NO in the second gas sample,
wherein said first channel means for controllably introducing the gas sample, said opaque sample cell, said first channel means for controllably delivering the gas sample, and said first channel detector capable of detecting an amount of NO define a first channel gas flow volume, and
said second channel means for controllably introducing the gas sample, said sample photolysis cell, said second channel means for controllably delivering the gas sample, and said second channel detector capable of detecting an amount of NO define a second channel gas flow volume,
said first channel gas flow volume and said second channel gas flow volume being minimal and equal.
22. A dual-channel photolysis system according to claim 21, wherein said reflector is ellipsoidal in shape.

23. A method of measuring a quantity of $NO_2$ in a gas sample with a single-channel photolysis system, said system comprising (i) a UV light source for emitting light capable of photolytically dissociating $NO_2$ in said gas sample to NO; (ii) a means for positioning said light source; (iii) an ellipsoidal reflector for collecting and focusing said light from the light source; (iv) an enclosure for enclosing said light source and said ellipsoidal reflector; (v) an optical filter assembly for receiving, filtering, and transmitting said focused light from the ellipsoidal reflector; (vi) a shutter capable of blocking the transmission of said filtered light which is transmitted through the optical filter assembly; (vii) a sample photolysis cell for containing a volume of said gas sample; (viii) a means for controllably introducing said gas sample to said sample photolysis cell, and a means for controllably delivering said gas sample from said sample photolysis cell; (ix) a detector capable of detecting an amount of said NO present in said gas sample delivered from the sample photolysis cell, and capable of emitting a signal representative of said amount of NO; and (x) a means for measuring said signal so as to quantify said amount of NO,
said method comprising the steps of:
(a) introducing a first portion of said gas sample to said sample photolysis cell;
(b) irradiating said first portion of the gas sample with said light capable of photolytically dissociating $NO_2$;
(c) delivering said first portion of the gas sample from said sample photolysis cell to said detector so as to detect said amount of NO present in the first portion of the gas sample, and so as to emit said signal representative of said first portion amount of NO;
(d) measuring said signal so as to quantify said first portion amount of NO;
(e) positioning said shutter so as to block the transmission of said filtered light to said sample photolysis cell;
(f) introducing a second portion of said gas sample to said sample photolysis cell;
(g) delivering said second portion of the gas sample from said sample photolysis cell to said detector so as to detect said amount of NO present in the second portion of the gas sample, and so as to emit said signal representative of said second portion amount of NO;
(h) measuring said signal so as to quantify said second portion amount of NO; and
(i) positioning said shutter so as to allow the transmission of said filtered light to said sample photolysis cell.

24. A method of measuring a quantity of $NO_2$ in a gas sample with a single-channel photolysis system according to claim 23, further comprising continuously repeating steps (a) through (i) one or a plurality of times.

25. A method of measuring a quantity of $NO_2$ in a gas sample with a single-channel photolysis system according to claim 23, wherein said means for controllably introducing the gas sample to the sample photolysis cell, said sample photolysis cell, and said means for controllably delivering the gas sample from the sample photolysis cell, each comprises a volume which minimizes a residence time of the gas sample in the system.

26. A method of measuring a quantity of $NO_2$ in a gas sample with a single-channel photolysis system according to claim 23, wherein said steps (a) through (i) are performed so as to minimize the gas sample residence time in the system.

27. A method of measuring a quantity of $NO_2$ with a dual-channel system, said system comprising a gas inlet line for receiving a total gas sample; a flow divider for dividing said total gas sample into a first gas sample having a first gas sample volume, and a second gas sample having a second gas sample volume, said first gas sample volume and said second gas sample volume being equal; a first channel for detecting ambient NO in said first gas sample; and a second channel for detecting both ambient NO, and NO resulting from the photolytic dissociation of $NO_2$ to NO, in said second gas sample, said first channel comprising (i) an opaque sample cell; (ii) a first channel means for controllably introducing said first gas sample to said opaque sample cell, and a first channel means for controllably delivering said first gas sample from said opaque sample cell; (iii) a first channel detector capable of detecting an amount of said NO present in the first gas sample delivered from the opaque sample cell, and capable of emitting a signal representative of said amount of NO in the first gas sample; and (iv) a first channel means for measuring said signal so as to quantify said amount of NO in the first gas sample, and said second channel comprising (v) a UV light source for emitting light capable of photolytically dissociating $NO_2$ in said second gas sample to NO; (vi) a means for positioning said light source; (vii) an ellipsoidal reflector for collecting and focusing said light from the light source; (viii) an enclosure for enclosing said light source and said ellipsoidal reflector; (ix) an optical filter assembly for receiving, filtering, and transmitting said focused light from the ellipsoidal reflector; (x) a shutter capable of blocking the transmission of said filtered light which is transmitted through the optical filter assembly; (xi) a sample photolysis cell for containing a volume of said second gas sample; (xii) a second channel means for controllably introducing said second gas sample to said sample photolysis cell, and a second channel means for controllably delivering said second gas sample from said sample photolysis cell; (xiii) a second channel detector capable of detecting an amount of said NO present in said second gas sample delivered from the sample photolysis cell, and capable of emitting a signal representative of said amount of NO in the second gas sample; and (xiv) a second channel means for measuring said signal so as to quantify said amount of NO in the second gas sample, wherein said first channel means for controllably introducing the gas sample, said opaque sample cell, said first channel means for controllably delivering the gas sample, and said first channel detector capable of detecting an amount of NO define a first channel gas flow volume, and said second channel means for controllably introducing the gas sample, said sample photolysis cell, said second channel means for controllably delivering the gas sample, and said second channel detector capable of detecting an amount of NO define a second channel gas flow volume, said first channel gas flow volume and said second channel gas flow volume being minimal and equal, said method comprising the steps of:
  in said first channel, (a) introducing said first gas sample to said opaque sample cell;
  (b) delivering said first gas sample from said opaque sample cell to said first channel detector so as to detect said amount of NO present in the first gas sample, and so as to emit said signal representative of said amount of NO in the first gas sample; and
  (c) measuring said signal so as to quantify said amount of NO in the first gas sample; and
  in said second channel,
  (d) introducing a first portion of said second gas sample to said sample photolysis cell;
  (e) irradiating said first portion of the second gas sample with said light capable of photolytically dissociating $NO_2$;
  (f) delivering said first portion of the second gas sample from said sample photolysis cell to said second channel detector so as to detect said amount of NO present in the first portion of the second gas sample, and so as to emit said signal representative of said first portion amount of NO;
  (g) measuring said signal so as to quantify said first portion amount of NO;
  (h) positioning said shutter so as to block the transmission of said filtered light to said sample photolysis cell;
  (i) introducing a second portion of said second gas sample to said sample photolysis cell;
  (j) delivering said second portion of the second gas sample from said sample photolysis cell to said second channel detector so as to detect said amount of NO present in the second portion of the second gas sample, and so as to emit said signal representative of said second portion amount of NO;
  (k) measuring said signal so as to quantify said second portion amount of NO; and
  (l) positioning said shutter so as to allow the transmission of said filtered light to said sample photolysis cell,
    wherein said steps (a) through (c) are performed simultaneous with said steps (d) through (l).

* * * * *